US006465633B1

(12) United States Patent
Skeiky

(10) Patent No.: US 6,465,633 B1
(45) Date of Patent: Oct. 15, 2002

(54) COMPOSITIONS AND METHODS OF THEIR USE IN THE TREATMENT, PREVENTION AND DIAGNOSIS OF TUBERCULOSIS

(75) Inventor: Yasir Skeiky, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/470,191

(22) Filed: Dec. 23, 1999

Related U.S. Application Data

(60) Provisional application No. 60/113,952, filed on Dec. 24, 1998.

(51) Int. Cl.$^7$ .................. C07H 21/04; A61K 39/04; A61K 31/7088
(52) U.S. Cl. ................ 536/23.7; 424/248.1; 514/44
(58) Field of Search .................... 536/23.1, 23.7; 514/44; 435/320.1, 375, 6, 69.1, 471, 490; 424/248.1

(56) References Cited

U.S. PATENT DOCUMENTS

| | | | |
|---|---|---|---|
| 3,943,119 | A | 3/1976 | Tsumita et al. |
| 4,689,397 | A | 8/1987 | Shinnick et al. |
| 4,879,213 | A | 11/1989 | Fox et al. |
| 4,952,395 | A | 8/1990 | Shinnick et al. |
| 5,108,745 | A | 4/1992 | Horwitz |
| 5,330,754 | A | 7/1994 | Kapoor et al. |
| 5,478,726 | A | 12/1995 | Shinnick et al. |
| 5,714,593 | A | 2/1998 | Laqueyrerie et al. |

FOREIGN PATENT DOCUMENTS

| | | |
|---|---|---|
| EP | 419 355 A1 | 3/1991 |
| WO | WO 88/05823 | 8/1988 |
| WO | WO 91/04272 | 4/1991 |
| WO | WO 91/14448 | 10/1991 |
| WO | WO 92/04049 | 3/1992 |
| WO | WO 92/14154 | 8/1992 |
| WO | WO 92/14823 | 9/1992 |
| WO | WO 92/21758 | 12/1992 |
| WO | WO 94/00493 | 1/1994 |
| WO | WO 95/01440 | 1/1995 |
| WO | WO 95/01441 | 1/1995 |
| WO | WO 95/14713 | 6/1995 |
| WO | WO 95/31216 | 11/1995 |
| WO | WO 96/15241 | 5/1996 |
| WO | WO 96/23885 | 8/1996 |
| WO | WO 97/09428 | 3/1997 |
| WO | WO 97/09429 | 3/1997 |
| WO | WO 98/16645 | 4/1998 |

OTHER PUBLICATIONS

Yamamoto (AU077540, GenCore, Jul. 30, 1999).*
Steinert (US Pat No. 5616500, Apr. 1, 1997, filed Apr. 30, 1993.*
Cole (Nature 393 (6685), 1998, pp. 537–544, Accession No. Z83864 A/123456).*
Gicquel (WO9909186, Feb. 25, 1999).*
Harman (WO94288, Oct. 27, 1994).*
Engel (WO9807868, Feb. 26, 1998).*
Eiglmeier (Mol. Microbol. 7(2), 197–206, 1993, Accession No. L78825.*
Content (US Pat. No. 5736524, Apr. 7, 1998, filed Nov. 14, 1994.*
Andersen "Effective Vaccination of Mice against *Mycobacterium tuberculosis* Infection with a Soluble Mixture of Secreted Mycobacterial Proteins" *Infection and Immunity* 62(6):2536–2544 (1994).
Anderson and Heron "Specificity of a Protective Memory Immune Response against *Mycobacterium tuberculosis*" *Infection and Immunity* 61(3):844–851 (1993).
Andersen et al. "Identification of Immunodominant Antigens during Infection with *Mycobacterium tuberculosis*" *Scand. J. Immunol.* 36:823–831 (1992).
Anderson and Hansen "Structure and Mapping of Antigenic Domains of Protein Antigen b, a 38,000–Molecular Weight Protein of *Mycobacterium tuberculosis*" *Infection and Immunity* 57(8):2481–2488 (1989).
Boesen et al. "Human T–Cell Responses to Secreted Antigen Fractions of *Mycobacterium tuberculosis*" *Infection and Immunity* 63(4):1491–1497 (1995).
Burgess et al. "Possible Dissociation of the Heparin–binding and Mitogenic Activities of Heparin–binding (Acidic Fibroblast) Growth Factor–1 from its Receptor–binding Activities by Site–Directed of a Single Lysine Residue" *J. Cell Biol.* 111:2129–2138 (1990).
Campos–Neto et al. "CD40 ligand is not essential for the development of cell–mediated immunity and resistance to *Mycobacterium tuberculosis*" *J. Immunol.* 160(5):2037–2041 (1998).
Cole et al. "Deciphering the biology of *Mycobacterium tuberculosis* from the complete genome sequence" *Nature* 393:537–544 (Jun. 1998).
Eiglmeier et al. "Use of an ordered cosmid library to deduce the genomic organization of *Mycobacterium leprae*" *Mol. Microbiol.* 7(2):197–206 (1993).
Fifis et al. "Purification and Characterization of Major Antigens from a *Mycobacterium bovis* Culture Filtrate" *Infection and Immunity* 59(3):800–807 (1991) (GenBank accession No. A47607).
Geysen et al. "Cognitive features of continuous antigenic determinants" *J. Mol. Recognition* 1:32–41 (1988).

(List continued on next page.)

Primary Examiner—John S. Brusca
Assistant Examiner—Marjorie A. Moran
(74) Attorney, Agent, or Firm—Townsend & Townsend and Crew LLP

(57) ABSTRACT

The present invention relates to Mycobacterium antigens, optionally from a species such as *M. tuberculosis, M. bovis, M. smegmatis,* BCG, *M. leprae, M. scrofulaceum, M avium-intracellulare, M. marinum, M. ulcerans, M. kansasii, M. xenopi, M. szulgai, M. fortuium,* or *M. chelonei.* In particular, the invention relates to M. tuberculosis secretory polypeptides, polynucleotides that encode the polypeptides, and methods of using such compositions in the treatment, prevention and diagnosis of *M. tuberculosis* infection.

7 Claims, No Drawings

OTHER PUBLICATIONS

Greenway et al. "Enhancement of protective immune responses to Venezuelan equine encephalitis (VEE) virus with microencapsulated vaccine" *Vaccine* 13:1411–1420 (1995).

Horwitz et al. "Protective immunity against tuberculosis induced by vaccination with major extracellular proteins of *Mycobacterium tuberculosis*" *Proc. Natl. Acad. Sci. USA* 92:1530–1534 (1995).

Kadival et al. "Radioimmunoassay of tuberculosis antigen" *Indian J. Med. Res.* 75:765–770 (1982).

Lazar et al. "Transforming Growth Factor α: Mutation of Aspartic Acid 47 and Leucine 48 results in Different Biological Activities" *Mol. Cell. Biol.* 8(3):1247–1252 (1988).

Lewinsohn et al. "Characterization of human CD8+ T cells reactive with Mycobacterium tuberculosis–infected antigen–presenting cells" *J. Exp. Med.* 187(10):1633–1640 (1988).

Lowrie et al. "Towards a DNA vaccine against tuberculosis" *Vaccine* 12(16):1537–1540 (1994).

Nagai et al. "Isolation and Partial Characterization of Major Protein Antigens in the Culture Fluid of *Mycobacterium tuberculosis*" *Infection and Immunity* 59(1):372–382 (1991).

Orme "Prospects for new vaccines against tuberculosis" *Trends in Microbiology* 3(10):401–404 (1995).

Pal and Horwitz "Immunization with extracellular proteins from *Mycobacterium tuberculosis* induces cell–mediated immune responses and substantial protective immunity in a guinea pig model of pulmonary tuberculosis" *Infection and Immunity* 60(11):4781–4792 (1992).

Philipp et al. "An integrated map of the genome of the tubercle bacillus, *Mycobacterium tuberculosis* H37Rv, and comparison with *Mycobacterium leprae*" *Proc Natl Acad Sci U S A*. 93(7):3132–3137 (1996).

Romain et al. "Preparation of Tuberculin Antigen L" *Ann. Inst. Pasteur/Microbiol.* 136B:235–248 (1985).

Sanderson et al. "Identification of a CD4+ T Cell–stimulating Antigen of Pathogenic Bacteria by Expression Cloning" *J. Exp. Med.* 182(6):1751–1757 (1995).

Wallis et al. "Indentification of Antigens of *Mycobacterium tuberculosis* Using Human Monoclonal Antibodies" *J. Clin. Invest.* 84:214–219 (1989).

Young et al. "Screening of a Recombinant Mycobacterial DNA Library with Polyclonal Antiserum and Molecular Weight Analysis of Expressed Antigens" *Infection and Immunity* 55(6):1421–1425 (1987).

* cited by examiner

COMPOSITIONS AND METHODS OF THEIR USE IN THE TREATMENT, PREVENTION AND DIAGNOSIS OF TUBERCULOSIS

CROSS-REFERENCES TO RELATED APPLICATIONS

The present application claims priority to U.S. Ser. No. 60/113,952, filed Dec. 24, 1998, herein incorporated by reference.

The present application is also related to U.S. Ser. No. 08/523,463, filed Sep. 1, 1995, now abandoned; U.S. Ser. No. 08/533,634, filed Sep. 22, 1995, now abandoned; U.S. Ser. No. 08/659,683, filed Jun. 5, 1996, now abandoned; U.S. Ser. No. 08/680,574, filed Jul. 12, 1996, now abandoned; U.S. Ser. No. 08/730,510, filed Oct. 11, 1996, now abandoned; U.S. Ser. No. 08/818,112, filed Mar. 13, 1997; U.S. Ser. No. 08/942,578, filed Oct. 1, 1997, now abandoned; U.S. Ser. No. 09/025,197, filed Feb. 18, 1998; and U.S. Ser. No. 09/072,967, filed May 5, 1998, each herein incorporated by reference.

The present application is also related to Ser. No. 08/523,435, filed Sep. 1, 1995, now abandoned; U.S. Ser. No. 08/532,136, filed Sep. 22, 1995, now abandoned; U.S. Ser. No. 08/658,800, filed Jun. 5, 1996, now abandoned; U.S. Ser. No. 08/680,573, filed Jul. 12, 1996, now abandoned; U.S. Ser. No. 08/729,622, filed Oct. 11, 1997, now abandoned; U.S. Ser. No. 08/818,111, filed Mar. 13, 1997; U.S. Ser. No. 08/942,341, filed Oct. 1, 1997, now abandoned; U.S. Ser. No. 09/024,753, filed Feb. 18, 1998; and U.S. Ser. No. 09/072,596, filed May 5, 1998, each herein incorporated by reference.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to *Mycobacterium tuberculosis* antigens. In particular, the invention relates to *M. tuberculosis* secretory polypeptides, polynucleotides that encode the polypeptides, and methods of using such compositions in the treatment, prevention and diagnosis of *M. tuberculosis* infection.

BACKGROUND OF THE INVENTION

Tuberculosis is a chronic infectious disease caused by infection with *M. tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination, and accurate early diagnosis of the disease are of utmost importance. Currently, vaccination with live bacteria is the most efficient method for inducing protective immunity. The most common Mycobacterium employed for this purpose is Bacillus Calmette-Guerin (BCG), an avirulent strain of *M. bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48–72 hours after injection, which indicates exposure to Mycobacteria antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in Acquired Immunodeficiency Syndrome patients, due to the depletion of $CD4^+$ T cells associated with human immunodeficiency virus (HIV) infection. Mycobacterium-reactive $CD4^+$ T cells have been shown to be potent producers of gamma-interferon (IFN-$\gamma$), which, in turn, has been shown to trigger the anti-mycobacterial effects of macrophages in mice. While the role of IFN-$\gamma$ in humans is less clear, studies have shown that 1,25-dihydroxy-vitamin D3, either alone or in combination with IFN-$\gamma$ or tumor necrosis factor-alpha, activates human macrophages to inhibit *M. tuberculosis* infection. Furthermore, it is known that IFN-$\gamma$ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan & Kaufmann, 1994, *Tuberculosis: Pathogenesis, Protection and Control*, Bloom (ed.), ASM Press, Washington, D.C.

Accordingly, there is a need for improved vaccines and diagnostic agents, as well as methods for preventing, treating and detecting tuberculosis. Although the genome of one strain of *M. tuberculosis* has been sequenced recently (Cole et al., 1998, *Nature* 393:537–544), it has not been determined which of the gene sequences would encode immunogenic or antigenic products. Thus, there remains a need for the identification and characterization of *M. tuberculosis* antigens suitable for use in the prevention, treatment and diagnosis of the disease.

SUMMARY OF THE INVENTION

The present invention relates to *M. tuberculosis* antigens. In particular, it relates to *M. tuberculosis* polypeptides, polynucleotides encoding the polypeptides, methods of using the polypeptides and polynucleotides in the diagnosis, treatment and prevention of *M. tuberculosis* infection.

The present invention is based, in part, on Applicants' discovery of a large number of polypeptides produced in a *M. tuberculosis* expression library that were reactive with an antiserum raised to *M. tuberculosis* polypeptides. Since the antiserum was generated against *M. tuberculosis* polypeptides that had been purified from bacterial culture supernatants, the antiserum preferentially reacted with bacterial secretory products. The antibody-reactive clones were isolated, and their nucleotide sequences were determined. Sequence comparison of these clones with publicly available gene sequences revealed that many of the isolated clones encoded previously unknown M. tuberculosis antigens. The nucleotide sequences of these coding sequences are recited in SEQ ID NOS:1–91, and their amino acid sequences can be deduced therefrom. Both the coding sequences and their encoded polypeptide products are suitable for a variety of uses.

In a specific embodiment of the invention, the isolated or purified M. tuberculosis polypeptides of the invention may be formulated as pharmaceutical compositions for administration into a subject in the prevention and/or treatment of *M. tuberculosis* infection. In that regard, the polypeptides may be used individually or in combination, including their use as fusion proteins. The immunogenicity of the antigens may be enhanced by the inclusion of an adjuvant.

It is also an object of the invention that the polypeptides be used in in vitro assays for detecting humoral antibodies or cell-mediated immunity against *M. tuberculosis* for diagnosis of infection or monitor of disease progression. Additionally, the polypeptides may be used as an in vivo diagnostic agent in the form of an intradermal skin test. Alternatively, the polypeptides may be used as immunogens to generate anti-*M. tuberculosis* antibodies in a non-human animal. The antibodies can be used to detect the target antigens in vivo and in vitro.

In another aspect of the invention, the isolated or purified polynucleotides are used to produce recombinant polypeptide antigens in vitro. Alternatively, the polynucleotides may be administered directly into a subject as DNA vaccines to cause antigen expression in the subject, and the subsequent induction of an anti-*M. tuberculosis* immune response. Additionally, the polynucleotides, portions thereof, or their complements may be used as molecular probes or primers to detect the presence of bacteria in a biologic sample.

BRIEF DESCRIPTION OF THE DRAWINGS

Not applicable.

DETAILED DESCRIPTION OF THE INVENTION

The present invention relates to Mycobacterium antigens, optionally from a species such as *M. tuberculosis, M. bovis, M. smegmatis,* BCG, *M. leprae, M. scrofulaceum, M. avium-intracellulare, M. marinum, M ulcerans, M kansasii, M. xenopi, M. szulgai, M fortuium,* or *M. chelonei.* In particular, the invention relates to *M. tuberculosis* secretory polypeptides and immunogenic fragments thereof, polynucleotides that encode the polypeptides and immunogenic fragments thereof, and methods of using such compositions in the treatment, prevention and diagnosis of *M. tuberculosis* infection. In one embodiment of the invention, the polypeptides of the invention are used to diagnose tuberculosis. In another embodiment of the invention, the polypeptides of the invention are used to induce an immune response in a patient in order to prevent tuberculosis or to reduce the probability of pathological responses typical of tuberculosis in a patient. In another embodiment of the invention, the polynucleotides of the invention are used to produce the polypeptides of the invention. In another embodiment, the polynucleotides of the invention are used to produce DNA vaccines, or for diagnostic purposes.

Definitions

As used herein, the following terms have the meanings ascribed to them unless specified otherwise.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095–35101 (1998).

The term "SEQ ID NOS:1–91" also encompasses degenerate nucleotide sequences encoding same the polypeptides.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

An isolated polypeptide comprising "an immunogenic portion of a polypeptide encoded by SEQ ID NOS:1–91" refers to a polypeptide fragment that is encoded by a at least a portion of one of the referenced sequences, but not necessarily the entire sequence.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline. γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the rUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Fusion polypeptide" or "fusion protein" refers to a protein having at least two heterologous polypeptides covalently linked, preferably Mycobacterium sp. polypeptides, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, subsequences, and interspecies homologs of the antigens that make up the fusion protein. *Mycobacterium tuberculosis* antigens are described in Cole et al., *Nature* 393:537 (1998).

The terms "identical" or percent "identity," in the context of two or more nucleic acids or polypeptide sequences, refer to two or more sequences or subsequences that are the same or have a specified percentage of amino acid residues or nucleotides that are the same (i.e., 60%, 65%, 70%, 75%, or 80% identity, preferably 85%, 90%, or 95% identity over a specified window region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al. *Nuc. Acids Res.* 25:3389–3402 (1977) and Altschul et al, *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached The BLAST algorithm parameters W, T, and X determine the sensitivity and speed of the alignment. The BLASTN program (for nucleotide sequences) uses as defaults a wordlength (.W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_1$–$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see, e.g., *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990))

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in Monoclonal *Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

Isolation of the Antigen Coding Sequences

The present invention relates to nucleic acid molecules that encode antigenic polypeptides of Mycobacterium sp., e.g., *M. tuberculosis*. In a specific embodiment by way of example, infra, a number of *M. tuberculosis* antigen coding sequences were isolated, and their nucleotide sequences characterized (SEQ ID NOS:1–91). In accordance with the invention, any nucleotide sequence which encodes the amino acid sequence of an isolated antigen can be used to generate recombinant molecules which direct the expression of the antigen coding sequence. Additionally, the invention also relates to a fusion polynucleotide between two or more coding sequences, e.g., two or more Mycobacterium antigen coding sequences.

In order to clone full-length coding sequences or homologous variants, labeled DNA probes designed from any portion of the nucleotide sequences or their complements disclosed herein may be used to screen a genomic or cDNA library made from various strains of *M. tuberculosis*. Isolation of coding sequences may also be carried out by the polymerase chain reactions (PCR) using two degenerate oligonucleotide primer pools designed on the basis of the coding sequences disclosed herein.

In addition, the invention relates to purified polynucleotides containing at least 15 nucleotides (i.e., a hybridizable portion) of an antigen coding sequence or its complement. In other embodiments, the polynucleotides contain at least 25 (continuous) nucleotides, 50 nucleotides, 100 nucleotides, 150 nucleotides, or 200 nucleotides of an antigen coding sequence, or a full-length antigen coding sequence. Nucleic acids can be single or double stranded. Such nucleic acids also encode variant forms of the antigens which retain reactivity with antibodies.

The invention also relates to isolated or purified polynucleotides complementary to the foregoing sequences and polynucleotides that selectively hybridize to such complementary sequences. In a specific embodiment, the polynucleotides contain at least 15, 25, 50, 100, or 200 nucleotides or the length of the entire antigen coding sequence. In a preferred embodiment, a polynucleotide which hybridizes to an antigen coding sequence (SEQ ID NOS:1–91) or its complementary sequence under conditions of low stringency is provided. By way of example and not limitation, exemplary conditions of low stringency are as follows (see also Shilo & Weinberg, 1981, *Proc. Natl. Acad. Sci. USA* 78:6789–6792): Filters containing DNA are pretreated for 6 h at 40° C. in a solution containing 35/%, formamide, 5×SSC, 50 mM Tris-HCl (pH 7.5), 5mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° W in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another preferred embodiment, a polynucleotide which hybridizes to an antigen coding sequence or its complementary sequence under conditions of high stringency is provided. By way of example and not limitation, exemplary conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for $^1$h in a solution containing 2×SSC, 0.01% PVP, 0.01% Ficoll, and 0.01% BSA. This is followed by awash in 0.1×SSC at 50° C. for 45 min before autoradiography. Other conditions of high stringency which may be used are well known in the art.

In yet another preferred embodiment, a polynucleotide which hybridizes to an antigen coding sequence or its complementary sequence under conditions of moderate stringency is provided. Exemplary conditions of moderate stringency are as follows: Filters containing DNA are pretreated for 6 h at 55° C. in a solution containing 6×SSC, 5×Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 h in a solution containing 2×SSC, 0.1% SDS.

Polypeptides Encoded by the Coding Sequences

In accordance with the invention, a polynucleotide of the invention which encodes an antigenic polypeptide, a variant polypeptide, peptide fragments, fusion proteins or functional equivalents thereof, may be used to generate recombinant nucleic acid molecules that direct the expression of the protein, the peptide fragments, fusion proteins or functional equivalents thereof, in appropriate host cells. The polypeptide products encoded by such polynucleotides may be naturally occurring or altered by molecular manipulation of the coding sequence.

Due to the inherent degeneracy of the genetic code, other DNA sequences which encode substantially the same or a functionally equivalent amino acid sequence, may be used in the practice of the invention for the expression of the antigenic polypeptides. Such DNA sequences include those which are capable of hybridizing to the coding sequences or their complements disclosed herein under low, moderate or high stringency conditions described, supra.

Altered nucleotide sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues, which result in a silent change thus producing a functionally equivalent antigenic epitope. Such conservative amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, seine, threonine and tyrosine; and amino acids with nonpolar head groups include alanine, valine, isoleucine, leucine, phenylalanine, proline, methionine and tryptophan.

The nucleotide sequences of the invention may be engineered in order to alter the antigen coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc.

In an alternate embodiment of the invention, the coding sequence of an antigen could be synthesized in whole or in part, using chemical methods well known in the art. See, e.g., Caruthers et al., 1980, *Nuc. Acids Res. Symp. Ser* 7:215–233; Crea & Horn, 1980, *Nuc. Acids Res.* 9(10):2331; Matteucci & Caruthers, 1980, *Tetrahedron Letter* 21:719; and Chow & Kempe, 1981, *Nuc. Acids Res.* 9(12):2807–2817. Alternatively, the polypeptide itself could be produced using chemical methods to synthesize an amino acid sequence in whole or in part. For example, peptides can be synthesized by solid phase techniques, cleaved from the resin, and purified by preparative high performance liquid chromatography. (See Creighton, 1983, *Proteins Structures And Molecular Principles,* W.H. Freeman and Co., N.Y. pp. 50–60). The composition of the synthetic polypeptides may be confirmed by amino acid analysis or sequencing (e.g., the Edman degradation procedure; see Creighton, 1983, *Proteins, Structures and Molecular Principles,* W.H. Freeman and Co., N.Y., pp. 34–49).

In a specific embodiment of the invention, a polypeptide containing at least 10 (continuous) amino acids of the antigen is provided. In other embodiments, the polypeptide may contain at least 20 or 50 amino acids of the antigen. In specific embodiments, such polypeptides do not contain more than 100, 150 or 200 amino acids. Derivatives or analogs of the polypeptides include, but are not limited to, molecules containing regions that are substantially homologous to the antigen or fragments thereof (e.g., in various embodiments, at least 60% or 70% or 80% or 90% or 95% identity over an amino acid sequence of identical size or when compared to an aligned sequence in which the alignment is done by a computer homology program known in the art) or product encoded by a polynucleotide that is capable of hybridizing to a naturally-occurring coding sequence, under highly stringent, moderately stringent, or low stringent conditions.

The derivatives and analogs of the invention can be produced by various methods known in the art. The manipulations which result in their production can occur at the nucleic acid or protein level. For example, a cloned coding sequence can be modified by any of numerous strategies known in the art (Maniatis, 1990, *Molecular Cloning, A Laboratory Manual*, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of a polynucleotide encoding a derivative or analog, care should be taken to ensure that the modified coding sequence remains within the same translational reading frame as the antigen, uninterrupted by translational stop signals, in the coding region where the antigenic epitope is encoded.

Additionally, the coding sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, et al., 1978, *J. Biol. Chem.* 253:655 1), use of TAB® linkers (Pharmacia), and the like.

Manipulations may also be made at the protein level. Included within the scope of the invention are protein fragments or other derivatives or analogs which are differentially modified during or after translation, e.g., by glycosylation, acetylation, phosphorylation, amidation, derivatization by known protecting/blocking groups, proteolytic cleavage, linkage to a cytokine or another antigen. Any of numerous chemical modifications may be carried out by known techniques, including but not limited to, specific chemical cleavage by cyanogen bromide, trypsin, chymotrypsin, papain, $V_8$ protease, $NaBH_4$; acetylation, formylation, oxidation, reduction; metabolic synthesis in the presence of tunicamycin; etc.

In addition, analogs and derivatives can be chemically synthesized. Nonclassical amino acids or chemical amino acid analogs can be introduced as a substitution or addition into the sequence. Non-classical amino acids include, but are not limited to, the D-isomers of the common amino acids, a-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-25 amino acids, designer amino acids such as n-methyl amino acids, Ca-methyl amino acids, Nα-methyl amino acids, and amino acid analogs in general. Furthermore, the amino acid can be D (dextrorotary) or L (levorotary).

In a specific embodiment, the derivative is a chimeric or fusion protein containing two or more antigens or a fragment thereof joined at its amino- or carboxy-terminus via a peptide bond. Alternatively, the antigens are connected by a flexible . polylinker such as Gly-Cys-Gly or Gly-Gly-Gly-Gly-Ser repeated 1 to 3 times (SEQ ID NO:92–97) (Bird et al., 1988, *Science* 242:423–426; Chaudhary et al., 1990, *Proc. Nat'l. Acad. Sci. U.S.A.* 87:1066–1070). In one embodiment, such a chimeric protein is produced by recombinant expression of a nucleic acid encoding the protein (an antigen coding sequence joined inframe to a coding sequence for another antigen or a heterologous protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of the antigen coding sequence fused to any other coding sequences may be constructed.

In another specific embodiment, the derivative is a molecule comprising a region of identity with the antigen. By way of example, in various embodiments, a protein region can be considered "substantially identical" to a second protein region when the amino acid sequence of the first region is at least 60%, 65%, 70%, 75%, 80%, 85%, 90%, or 95% identical, when compared to any sequence in the second region of an equal number of amino acids as the number contained in the first region or when compared to an aligned sequence of the second region that has been aligned by a computer homology program know n in the art, and as described herein.

Production of *M. tuberculosis* Polypeptides

In order to produce a *M. tuberculosis* antigen of the invention the nucleotide sequence coding for the antigen, or a functional equivalent, is inserted into an appropriate expression vector, i.e., a vector which contains the necessary elements for the transcription and translation of the inserted coding sequence. The antigen as well as host cells or cell lines transfected or transformed with recombinant expression vectors can be used for a variety of purposes. These include, but are not limited to, large scale production of antigenic proteins.

Methods which are well known to those skilled in the art can be used to construct expression vectors containing an antigen coding sequence and appropriate transcriptional/translational control signals. These methods include in vitro recombinant DNA techniques, synthetic techniques and in vivo recombination/genetic recombination. (See, e.g., the techniques described in Sambrook et al., 1989, *Molecular Cloning A Laboratory Manual*, Cold Spring Harbor Laboratory, N.Y. and Ausubel et al., 1989, *Current Protocols in Molecular Biology*, Greene Publishing Associates and Wiley Interscience, N.Y.). RNA capable of encoding a polypeptide may also be chemically synthesized (Gait, ed., 1984, *Oligonucleoide Synthesis*, IRL Press, Oxford).

A. Expression Systems

A variety of host-expression vector systems may be utilized to express an antigen coding sequence. These include, but are not limited to, microorganisms such as bacteria (e.g., *E. coil, B. subtilis*, Mycobacterium sp) transformed with recombinant bacteriophage DNA, plasmid DNA or cosmid DNA expression vectors containing an antigen coding sequence; yeast (e.g., Saccharomyces, Pichia) transformed with recombinant yeast expression vectors containing an antigen coding sequence; insect cell systems infected with recombinant virus expression vectors (e.g., baculovirus) containing an antigen coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing an antigen coding sequence; or mammalian cell systems (e.g., COS, CHO, BHK, 293, 3T3 cells). The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of a the antigen coding sequence, SV40-, BPV- and EBV-based vectors may be used with an appropriate selectable marker.

Bacterial systems are preferred for the expression of *M. tuberculosis* antigens. For in vivo delivery, a bacterium such as Bacillus Calmette-Guerin or *E. coli* may be engineered to express a specific antigenic polypeptide of the invention on its cell surface. A number of other bacterial expression vectors may be advantageously selected depending upon the use intended for the expressed products. For example, when large quantities of the antigen are to be produced for the generation of antibodies or formulation of pharmaceutical compositions, vectors which direct the expression of high levels of fusion protein products that are readily purified may be desirable. Such vectors include, but are not limited to, the *E. coli* expression vector pUR278 (Ruther et al., 1983, *EMBO J.* 2:1791), in which an antigen coding sequence may be ligated into the vector in frame with the lacZ coding region so that a hybrid protein is produced; pIN vectors (Inouye & Inouye, 1985, *Nucleic Acids Res.* 13:3101–3109; Van Heeke & Schuster, 1989, *J. Biol. Chem.* 264:5503–5509); and the like. pGEX vectors may also be used to express foreign polypeptides as fusion proteins with glutathione 5-transferase (GST). In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

B. Purification of the Polypeptides

Once a recombinant protein is expressed, it can be identified by assays based on the physical or functional properties of the product, including radioactive labeling of the product followed by analysis by gel electrophoresis, radioimmunoassay, ELISA, bioassays, etc.

Once the encoded protein is identified, it may be isolated and purified by standard methods including chromatography (e.g., high performance liquid chromatography, ion exchange, affinity, and sizing column chromatography), centrifugation, differential solubility, or by any other standard technique for the purification of proteins. The actual conditions used will depend, in part, on factors such as net charge, hydrophobicity, hydrophilicity, etc., and will be apparent to those having skill in the art. The functional properties may be evaluated using any suitable assay such as antibody binding, induction of T cell proliferation, stimulation of cytokine production such as IL-2, IL4, IL-12 and IFN-γ. For the practice of the present invention, it is preferred that each antigen is at least 80% purified from other proteins. It is more preferred that they are at least 90% purified. For in vivo administration, it is preferred that the proteins are greater than 95% purified.

In another alternate embodiment, native proteins can be purified from natural sources, by standard methods such as those described above (e.g., immunoaffinity purification). In a specific embodiment of the present invention, the antigenic polypeptides, whether produced by recombinant DNA techniques or by chemical synthetic methods or by purification from natural sources include, but are not limited to, those containing, as a primary amino acid sequence, all or part of the amino acid sequences deduced from the nucleotide sequences recited in SEQ ID NOS:1–91, as well as fragments and other derivatives, and analogs thereof, including proteins homologous thereto.

Production of Antibodies

Also within the scope of the present invention are antibodies that specifically recognize one or more epitopes of a polypeptide of the invention. Such antibodies include, but are not limited to, polyclonal antibodies, monoclonal antibodies (mAbs), humanized antibodies, chimeric antibodies, single chain antibodies, fragments produced by a Fab expression library, anti-idiotypic (anti-Id) antibodies, and epitope-binding fragments of any of the above such as Fab and $F(ab')_2$.

The antibodies of the invention may be used, for example, in the detection of the polypeptide of the invention in a biological sample and may, therefore, be utilized as part of a diagnostic or prognostic technique, for example, to test whether a person is infected with *M. tuberculosis*. Such antibodies may also be used to inhibit or kill the bacteria or bacterial infected cells. Thus, such antibodies are useful for therapy and diagnosis of tuberculosis.

For the production of antibodies, various host animals may be immunized by injection with a polypeptide. Such host animals may include, but are not limited to, rabbits, hamsters, mice, and rats. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (Bacillus Calmette-Guerin) and *Coryne bacterium parvum.* Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, *Nature* 256:495–497; and U.S. Pat. No. 4,376,110), the human B-cell hybridoma technique (Kosbor et al., 1983, *Immunology* Today 4:72; Cole et al., 1983, *Proc. Natl. Acad. Sci. USA* 80:2026–2030), and the EBV-hybridoma technique (Cole et al., 1985, *Monoclonal Antibodies And Cancer Therapy*, Alan R. Liss, Inc., pp. 77–96). Such antibodies may be of any immunoglobulin class including, but not limited to, IgG, IgM, IgB, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, *Proc. Natl. Acad. Sci. USA*, 81:6851–6855; Neuberger et al., 1984, *Nature*, 3 12:604–608; Takeda et al., 1985, *Nature*, 3 14:452–454) by splicing the genes from a mouse antibody molecule of appropriate antigen specificity together with genes from a human antibody molecule of appropriate biological activity can be used. A chimeric antibody is a molecule in which different portions are derived from different animal species, such as, for example, those having a variable region derived from a mouse mAb and a human immunoglobulin constant region. Humanized antibodies may be generated according to the methods described in U.S. Pat. Nos. 5,693,762; 5,585,089; and 5,565,332.

Alternatively, techniques described for the production of single chain antibodies (U.S. Pat. No. 4,946,778; Bird, 1988, *Science* 242:423–426; Huston et al., 1988, *Proc. Natl. Acad. Sci. USA.* 85:5879–5883; and Ward et al., 1989, *Nature* 334:544–546) can be adapted to produce single chain antibodies against gene products of interest. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, *Science,* 246:1275–1281) to allow rapid and easy identification of monoclonal Fab fragments with the desired specificity.

Antibodies to the polypeptides of the invention can, in turn, be utilized to generate anti-idiotype antibodies that mimic an epitope of the polypeptide of interest, using techniques well known to those skilled in the art. (See, e.g., Greenspan & Bona, 1993, *FASEB J* 7(5):437–444; and Nissinoff, 1991, *J. Immunol.* 147(8):2429–2438). For example, antibodies which competitively inhibit the binding of an antibody to an antigenic peptide may mimic the antigenic epitope of the peptide. Such neutralizing anti-idiotypes or Fab fragments of such anti-idiotypes can be used in a subject to prime an immune response to the specific antigenic epitope.

Uses of an Antigen Coding Sequences

A polynucleotide encoding an antigenic polypeptide of the invention may be used for diagnostic, therapeutic and prophylactic purposes.

A. Diagnostic Uses

The polynucleotides of the invention may be used for diagnosis of tuberculosis in the detection of polynucleotide sequences specific to *M. tuberculosis* in a patient. Such detection may be accomplished, for example, by isolating polynucleotides from a biological sample obtained from a patient suspected of being infected with the bacteria. Upon isolation of polynucleotides from the biological sample, a labeled polynucleotide of the invention that is complementary to one or more of the polynucleotides, will be allowed to hybridize to polynucleotides in the biological sample using techniques of nucleic acid hybridization known to those of ordinary skill in the art. For example. such hybridization may be carried out in solution or with one hybridization partner on a solid support.

In another aspect, the oligonucleotide primers may be constructed that represent a sequence of one of the polynucleotides of the invention. By using two or more of such primers, for example, one may detect the presence of polynucleotide sequences specific for *M. tuberculosis* in a biological sample using, for example, the PCR.

In yet another aspect, oligonucleotides that represent a sequence of one of the polynucleotides of the invention may be used in an oligonucleotide ligation assay ("OLA") to detect a polynucleotide specific for *M. tuberculosis* in a biological sample. Alternatively, such an OLA assay may be used to detect a mutation in a polynucleotide specific for *M. tuberculosis* and, thus, a mutant strain of *M. tuberculosis.*

In another aspect, the polynucleotides of the invention are useful for the production of polypeptides of the invention. Such production may occur in vitro or in vivo. For example, using techniques of gene therapy described above, one may produce a polypeptide of the invention in an organism like, for example, a human. By producing a polypeptide of the invention in vivo, one can induce an immune response in the recipient.

B. Therapeutic or Prophylactic Uses of a Polynucleotide

The antigen coding sequence may be used to encode a protein product for use as an immunogen to induce and/or enhance immune responses to *M. tuberculosis.* In addition, such coding sequence may be ligated with a coding sequence of another antigen or a cytokine to construct a fusion polynucleotide. A fusion polynucleotide may also be used to express a recombinant protein for use as an immunogen containing multiple epitopes. Such polynucleotides may be used in vivo as a DNA vaccine (U.S. Pat. Nos. 5.589,466; 5,679,647; 5,703,055). In this embodiment of the invention, the polynucleotide expresses its encoded protein in a recipient to directly induce an immune response. The polynucleotide may be injected into a naive subject to prime an immune response to its encoded product, or administered to an infected or immunized subject to enhance the secondary immune responses.

In a preferred embodiment, a therapeutic composition comprises an antigen coding sequence or fragments thereof that is part of an expression vector. In particular, such a polynucleotide contains a promoter operably linked to the coding region, said promoter being inducible or constitutive, and, optionally, tissue-specific. In another embodiment, a polynucleotide contains a coding sequence flanked by regions that promote homologous recombination at a desired site in the genome, thus providing for intrachromosomal expression of the coding sequence (Koller & Smithies, 1989, *Proc. Natl. Acad. Sci. USA* 86:8932–8935; Zijlstra et al., 1989, *Nature* 342:435–43 8).

Delivery of the nucleic acid into a subject may be either direct, in which case the subject is directly exposed to the nucleic acid or nucleic acid-carrying vector, or indirect, in which case, cells are first transformed with the nucleic acid in vitro, then transplanted into the subject. These two approaches are known, respectively, as in vivo or ex vivo gene transfer.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (See, e.g., Wu & Wu, 1987, *J. Biol. Chem.* 262:4429–4432) which can be used to target cell types specifically expressing the receptors, etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (See, e.g., PCT Publications WO 92/06180 dated Apr. 16, 1992; WO 92/22635 dated Dec. 23, 1992; W092/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller & Smithies, 1989, *Proc. Natl. Acad. Sci. USA* 86:8932–8935; Zijlstra et al., 1989, *Nature* 342:435–438).

In a specific embodiment, a viral vector such as a retroviral vector can be used (see, e.g. Miller et al., 1993, *Meth. Enzymol.* 217:581–599). Retroviral vectors have been modified to delete retroviral sequences that are not necessary for packaging of the viral genome and integration into host cell DNA. An antigen coding sequence is cloned into the vector, which facilitates delivery of the nucleic acid into a recipient. More detail about retroviral vectors can be found in Boesen et al., 1994, *Biotherapy* 6:291–302, which describes the use of a retroviral vector to deliver the mdrI gene to hematopoietic stem cells in order to make the stem cells more resistant to chemotherapy. Other references illustrating the use of retroviral vectors in gene therapy are: Clowes et al., 1994, *J. Clin. Invest.* 93:644–651; Kiem et al., 1994, *Blood* 83:1467–1473; Salmons & Gunzberg, 1993, Human Gene Therapy 4:129–141; and Grossman & Wilson, 1993, *Curr. Opin. in Genetics and Devel.* 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Adeno-associated virus (AAV) has also been proposed for use in in vivo gene transfer (Walsh et al., 1993, *Proc. Soc. Exp. Biol. Med.* 204:289–300.

Another approach involves transferring a construct to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler & Behr, 1993, *Meth. Enzymol.* 217:599–618; Cohen et al., 1993, *Meth. Enzymol.* 217:618–644; Cline, 1985, *Pharmac. Ther.* 29:69–92) and may be used in accordance with the present invention.

Uses of the Antigenic Polypeptides

A. Diagnostic Uses Of A Polypeptide

The antigenic polypeptides of the invention are useful in the diagnosis of tuberculosis infection in vitro and in vivo.

The ability of a polypeptide of the invention to induce cell proliferation can be evaluated by contacting the cells, like, for example, T cells or NK cells or both, with the polypeptide and measuring the proliferation of the cells. The amount of polypeptide that is sufficient for evaluation of about $10^5$ cells may range, for example, from about 10 ng/mL to about 100 $\mu$g/mL and preferably is about 10 $\mu$g/mL. The incubation of a polypeptide with cells may be performed according to procedures known to those skilled in the art, for example, at about 37° C. for about six days. Following incubation with a polypeptide, the cells are assayed for a proliferative response, which may be evaluated by methods known to those of ordinary skill in the art, such as, for example, exposing cells to a pulse of radiolabeled thymidine and measuring the incorporation of label into cellular DNA. Preferably, a polypeptide that results in at least about a three fold increase in proliferation above background, i.e., the proliferation observed for cells cultured without polypeptide, is able to induce proliferation.

The ability of a polypeptide to stimulate the production of interferon-y or interleukin-12 r both, in cells may be evaluated, for example, by contacting the cells with the polypeptide and measuring the level of interferon-$\gamma$ or interleukin-12 produced by the cells. The amount of polypeptide that is sufficient for the evaluation of about $10^5$ cells may range, for example, from about 10 ng/mL to about 100 $\mu$g/mL and preferably is about 10 $\mu$g/mL. The polypeptide may be, but need not be, immobilized on a solid support, such as, for example, a bead or a biodegradable microsphere, such as those described in U.S. Pat. Nos. 4,897,268 and 5,075,109, both of which are incorporated herein by reference. The incubation of a polypeptide with cells may be performed according to, procedures known to those skilled in the art, for example, at about 37° C. for about six days. The incubation of a polypeptide with the cells may be performed according to procedures known to those skilled in the art, for example, at about 37° C. for about six days. Following incubation of cells with a polypeptide, one may assay for interferon-y or interleukin-12, or one or more subunits thereof, by using methods known to those of ordinary skill in the art, such as, for example, an enzyme-linked immunosorbent assay (ELISA) or, in the case of IL-12 p70 subunit, a bioassay such as, for example, an assay measuring proliferation of T cells. A polypeptide that results in the production of preferably at least about 50 $\mu$g of interferon-$\gamma$ per mL of cultured supernatant, containing about $10^4$–$10^5$ T cells per mL, is able to stimulate the production of interferon-$\gamma$. A polypeptide that stimulates the production of at least about 10 pg/mL of IL-12 $p^{70}$ subunit, or at least about 100 pg/mL of IL-12 p40 subunit, per about $10^5$ macrophages or B cells, or per about $3\times10^5$ PBMC, is able to stimulate the production of IL-12.

In another aspect, this invention provides methods for using one or more of the polypeptides to diagnose tuberculosis using a skin test in vivo. As used herein, a skin test is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide with dermal cells of the patient, such as, for example, a tuberculin syringe or 1 mL syringe. Preferably, the reaction is measured at least about 48 hours after injection, more preferably about 48 to about 72 hours after injection.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection, which may or may not be manifested as an active disease.

The polypeptides of this invention are preferably formulated, for use in a skin test, as pharmaceutical compositions containing a polypeptide and a physiologically acceptable carrier, as described, infra. Such compositions typically contain one or more of the above polypeptides in an amount ranging from about 1 $\mu$g to about 100 $\mu$g, preferably from about 10 $\mu$g to about 50 $\mu$g in a volume of 0.1 mL. Preferably, the carrier employed in such pharmaceutical compositions is a saline solution with appropriate preservatives, such as phenol and/or Tween 80™.

In another aspect, the present invention provides methods for using the polypeptides to diagnose tuberculosis. In this aspect. methods are provided for detecting *M. tuberculosis* infection in a biological sample using one or more of the polypeptides alone or in combination. As used herein, a "biological sample" is any antibody-containing sample obtained from a patient. Preferably, the sample is whole blood, sputum, serum. plasma, saliva cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample relative to a predetermined cut-off value. The presence of such antibodies indicates previous sensitization to mycobacterial antigens which may be indicative of tuberculosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *M. tuberculosis*. After determining which samples test positive (as described below) with each polypeptide, combinations of two or more polypeptides may be formulated that are capable of detecting infection in most, or all, of the samples tested. Such polypeptides are complementary. Approximately 25–30% of sera from tuberculosis-infected individuals are negative for antibodies to any single protein. Complementary polypeptides may, therefore, be used in combination to improve sensitivity of a diagnostic test.

There are a variety of assay formats known to those of ordinary skill in the art for using one or more polypeptides to detect antibodies in a sample. See, e.g., Harlow & Lane, *Antibodies: A Laboratory Manual,* Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases. adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook. 1991, at A12–A13).

In certain embodiments, the assay is an enzyme linked immunosorbent 15 assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (for example, Protein A, Protein G, lectin or free antigen) conjugated to a reporter group. Preferred reporter groups include enzymes (such as horseradish peroxidase), substrates, cofactors, inhibitors, dyes, radionuclides, luminescent groups, fluorescent groups, biotin and colloidal particles, such as colloidal gold and selenium. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford. Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time). followed by spectroscopic or other analysis of the reaction products.

To determine the presence or absence of anti-*M. tuberculosis* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for tuberculosis. In an alternate preferred embodiment, the cut-off value is determined using a Receiver Operator Curve, according to the method of Sackett et al., 1985, *Clinical Epidemiology. A Basic Science for Clinical Medicine,* Little Brown and Co., pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*M. tuberculosis* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 5 ng to about 1 $\mu$g, and more preferably from about 50 ng to about 500 ng. Such tests can typically be performed with a very small amount (e.g., one drop) of patient serum or blood.

B. Therapeutic and Prophylactic Uses of a Polypeptide

Purified or partially purified polypeptides or fragments thereof may be formulated as a vaccine or therapeutic composition. Such composition may include adjuvants to enhance immune responses. In addition, such proteins may be further suspended in an oil emulsion to cause a slower release of the proteins in vivo upon injection. The optimal ratios of each component in the formulation may be determined by techniques well known to those skilled in the art.

Any of a variety of adjuvants may be employed in the vaccines of this invention to enhance the immune response. Most adjuvants contain a substance designed to protect the antigen from rapid catabolism, such as aluminum hydroxide or mineral oil, and a specific or nonspecific stimulator of immune responses, such as lipid A, *Bortadella pertussis* or *Mycobacterium tuberculosis.* Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS1c, SBAS2 (Ling et al., *Vaccine* 15:1562–1567 (1997)), SBAS7, Al(OH)$_3$ and CpG oligonucleotide (WO96/02555).

In the vaccines of the present invention, it is preferred that the adjuvant induces an immune response comprising Th1 aspects. Suitable adjuvant systems include, for example, Montanide ISA 720 (Seppic, France), SAF (Chiron, USA), QS-21 and other saponin-like materials (Aquila, USA), ISCOMS (CSL), MF-59 (Chiron, USA), SBAS series of adjuvants (Smith Kline, Belguim), MPL (Corixa, USA), Detox (Corixa, USA), RC-529 (Ribi. USA), aminoalkyl glucosaminide 4-phosphates (AGPs) and other synthetic MPL-like adjuvants (Corixa, USA). Other adjuvant systems include a combination of monophosphoryl lipid A, preferably 3-de-O-acylated monophosphoryl lipid A (3D-MPL, optionally together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and is a preferred formulation.

Such a formulation may be administered to a subject per se or in the form of a pharmaceutical or therapeutic composition. Pharmaceutical compositions comprising the proteins may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the polypeptides into preparations which can be used pharmaceutically. Proper formulation is dependent upon the route of administration chosen.

For topical administration, the proteins may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration.

For injection, the proteins may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

For transmucosal administration, penetrants appropriate to the baffler to be permeated> are used in the formulation. Such penetrants are generally known in the art.

For oral administration, a composition can be readily formulated by combining the proteins with pharmaceutically acceptable carriers well known in the art. Such carriers enable the proteins to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the proteins may take the form of tablets, lozenges, etc. formulated in conventional manner.

For administration by inhalation, the proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the proteins and a suitable powder base such as lactose or starch.

The proteins may also be formulated in rectal or vaginal compositions such as suppositories or retention enemas, e.g., containing conventional suppository bases such as cocoa butter or other glycerides.

In addition to the formulations described previously, the proteins may also be formulated as a depot preparation. Such long acting formulations may be administered by implantation (for example subcutaneously or intramuscularly) or by intramuscular injection. Thus, for example, the proteins may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver an antigen. Certain organic solvents such as dimethylsulfoxide also may be employed, although usually at the cost of greater toxicity. Additionally, the proteins may be delivered using a sustained-release system, such as semipermeable matrices of solid polymers containing the therapeutic or vaccinating agent. Various sustained-release materials have been established and are well known by those skilled in the art. Sustained-release capsules may, depending on their chemical nature, release the proteins for a few weeks up to over 100 days. Depending on the chemical nature and the biological stability of the reagent, additional strategies for protein stabilization may be employed.

Determination of an effective amount of the antigen for administration is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the polypeptides and/or polynucleotides of the invention may be administered in about 1 to 3 doses for a 1–36 week period. Preferably, 3 doses are administered, at intervals of about 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from M. tuberculosis infection for at least 1–2 years. In general, the amount of polypeptide present in a dose (or produced in situ by the DNA in a dose) ranges from about1 pg to about 100 mg per kg of host, typically from about 10 µg to about 1 mg, and preferably from about 100 pg to about 1 pg. Suitable dose range will vary with the size of the patient, but will typically range from about 0.1 mL to about 5 mL.

The invention having been described, the following examples are offered by way of illustration and not limitation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLE

Isolation of Coding Sequences for M. tuberlucosis Antigens by Expression Cloning This example illustrates the preparation of M. tuberculosis soluble polypeptides from culture filtrate and the use of the polypeptides as immunogens for the generation of a rabbit antiserum. The antiserum was used in the screening of a M. tuberculosis expression library in order to identify antibody-reactive clones.

A. Materials and Methods

Purification of Polypeptides from M. Tuberculosis Culture Filtrate

M. tuberculosis (Erdman strain) was cultured in sterile GAS media at 37° C. or fourteen days. The media was then vacuum filtered (leaving the bulk of the cells) through a 0.45 µ filter into a sterile 2.5 L bottle. The media was next filtered through a 2 µ filter into a sterile 4 L bottle and $NaN_3$ was added to the culture filtrate to a concentration of 0.04%. The bottles were then placed in a 4° C. cold room.

The culture filtrate was concentrated by placing the filtrate in a 12 L reservoir that had been autoclaved and feeding the filtrate into a 400 mL Amicon stir cell which had been rinsed with ethanol and contained a 10,000 kDa MWCO membrane. The pressure was maintained at 60 psi using nitrogen gas. This procedure reduced the 12 L volume to approximately 50 mL.

The culture filtrate was dialyzed into 0.1% ammonium bicarbonate using a 8,000 kDa MWCO cellulose ester membrane, with two changes of ammonium bicarbonate solution. Protein concentration was then determined by a commercially available BCA assay (Pierce, Rockford, Ill.).

The dialyzed culture filtrate was then lyophilized, and the polypeptides resuspended in distilled water. The polypeptides were dialyzed against 0.01 mM 1,3 bis[tris (hydroxymethyl)-methylamino]propane, pH 7.5 (Bis-Tris propane buffer), the initial conditions for anion exchange chromatography. Fractionation was performed using gel profusion chromatography on a POROS 146 II Q/M anion exchange column 4.6 mm×100 mm (Perspective BioSystems, Framingham, Mass.) equilibrated in 0.01 mM Bis-Tris propane buffer pH 7.5. Polypeptides were eluted with a linear 0–0.5 M NaCl gradient in the above buffer system. The column eluent was monitored at a wavelength of 220 nm.

The pools of polypeptides eluting from the ion exchange column were dialyzed against distilled water and lyophilized. The resulting material was dissolved in 0.1% trifluoroacetic acid (TFA) pH 1.9 in water, and the polypeptides were purified on a Delta-Pak C18 column (Waters, Milford, Mass.) 300 Angstrom pore size, 5 micron particle size (3.9×150 mm). The polypeptides were eluted from the column with a linear gradient from 0–60% dilution buffer (0.1% TFA in acetonitrile). The flow rate was 0.75 mL/minute and the HPLC eluent was monitored at 214 nm. Fractions containing the eluted polypeptides were collected to maximize the purity of the individual samples. The procedure produced over 200 polypeptides from M. tuberculosis culture supernatants.

Generation of Rabbit Antiserum Against M. tuberculosis Polypeptides

Secretory proteins purified from M. tuberculosis culture filtrate were used to immunize rabbits for the generation of an antiserum. About 200 µg of the protein mixture in a volume of 2 mL containing 10 µg muramyl dipeptide (Calbiochem, La Jolla, Calif.) were mixed with 1 mL of incomplete Freund's adjuvant and injected into a rabbit subcutaneously. Four weeks later, the rabbit was boosted subcutaneously with 100 µg antigen preparation in incomplete Freund's adjuvant. Four weeks later, the rabbit received 50 µg of antigen preparation intravenously. The rabbits were bled and their sera prepared according to conventional procedures.

Screening of a M. tuberculosis Expression Library

Genomic DNA from M. tuberculosis Erdman strain was randomly sheared to an average size of 2 kb, and blunt ended with Klenow polymerase, followed by the addition of EcoRI adaptors. The insert was subsequently ligated into the Screen phage vector (Novagen, Madison, Wis.) and packaged in vitro using the PhageMaker extract (Novagen).

The resultant library was screened with rabbit antiserum raised against M. tuberculosis culture filtrate polypeptides. The clones reactive with the antiserum were selected for further analysis.

B. Results

In order to isolate coding sequences for secretory proteins of M. tuberculosis or proteins shed by the bacteria, supernatants of M. tuberculosis cultures were collected, filtered and concentrated, and the proteins contained therein were purified by ion exchange chromatography. The pool of purified polypeptides were used to immunize rabbits to raise an antiserum. The antiserum was used to screen an expression library constructed from genomic nucleotide sequences of M. tuberculosis.

The antiserum reacted with about 300 individual clones of the expression library. In contrast, screening with the antiserum of an expression library constructed with the lambda ZAP expression system (Stratagene, La Jolla, Calif.) produced only about 20 positive clones. Since *M. tuberculosis* culture filtrate contained over 250 polypeptides, it is believed that the expression cloning system disclosed in the present invention isolated the coding sequences for the majority of polypeptides in the culture filtrate. The isolated clones were sequenced and compared with known proteins in publicly available databases. Among these clones, ninety-one were determined to be novel, and their nucleotide sequences are shown in SEQ ID NOS:1–91. Since these clones were selected by reactivity with an antibody, they encoded products that contained antigenic epitopes. In addition, such products are also expected to be useful as immunogens to induce an immune response.

The present invention is not to be limited in scope by the exemplified embodiments or deposited organisms which are intended as illustrations of single aspects of the invention, and any clones, nucleotide or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

What is claimed is:

1. An isolated mycobacterial polynucleotide that hybridizes under highly stringent conditions to the complement of a polynucleotide consisting of a nucleotide sequence of SEQ ID NO:14 or SEQ ID NO:22, wherein the hybridization reaction is incubated at 65° C. in a solution comprising 6×SSC, and washed at 50° C. in a solution comprising 0.1×SSC.

2. An isolated polynucleotide of claim 1 that hybridizes under moderately stringent conditions to the complement of a polynucleotide consisting of a nucleotide sequence of SEQ ID NO:14 or SEQ ID NO:22, wherein the hybridization reaction is incubated at 55° C. in a solution comprising 6×SSC, and washed at 60° C. in a solution comprising 1×SSC and 0.1% SDS.

3. An isolated polynucleotide of claim 1, the isolated polynucleotide comprising a nucleotide sequence of SEQ ID NO:14 or SEQ ID NO:22.

4. A pharmaceutical composition comprising the isolated polynucleotide of claim 1.

5. A cell comprising the isolated polynucleotide of claim 1.

6. The cell of claim 5, which is a prokaryote.

7. The cell of claim 5, which is a eukaryote.

* * * * *

SEQUENCE LISTING

```
<160> NUMBER OF SEQ ID NOS:  97

<210> SEQ ID NO 1
<211> LENGTH: 270
<212> TYPE: DNA
<213> ORGANISM: Mycobacterium tuberculosis
<220> FEATURE:
<221> NAME/KEY: modified_base
<222> LOCATION: (1)...(270)
<223> OTHER INFORMATION: n = any nucleotide

<400> SEQUENCE: 1
ccacgacgtc taccgacgcg tcgggcaatg gcagctcggc caggtttgct tgcatcacct     60
ccactcgggg atagcggctc cggacatggg ccaccgcagt ctcgtcgtag tccaccgcga    120
tgacctggcg agcgacgcag gcgatcaggt cggcgccata tccctcgccg cagccggctt    180
ccancacgtc gcgggccgtg cagcggggtg ccagccgctg gtanacgaac tggtggcggc    240
gaaaccagta gttctcgatg tccagatcgg                                     270

<210> SEQ ID NO 2
<211> LENGTH: 613
<212> TYPE: DNA
<213> ORGANISM: Mycobacterium tuberculosis
<220> FEATURE:
<221> NAME/KEY: modified_base
<222> LOCATION: (1)...(613)
<223> OTHER INFORMATION: n = any nucleotide

<400> SEQUENCE: 2
gggcatatgc ctggcgagat gatgcgcnac atcaactgcg tgcaactacc gtcacggctt     60
gngcggtgta ccggtcatta cgccggcacg ggtccgcggc tttcatgctg cgggacccaa    120
ttgcatgcct ggaccgtcaa caaacccnat ntgatgcaca cccttctcna catggacttg    180
nacggcatca tcaccnatcg cgcgnaccta cttcgtgatg tnctcatcgc ccgcggcaag    240
tgggacggcc ctaaaanccc ggcnacaccg gaaacggtca gggcatgcgg atcggatcat    300
cgggatgcgn actcagcggc gtggtctcaa tggtcatcca gccagcaacc ggtagcaatc    360
ccaggatggc catcagcncg ccagggtcgc nagcccccac acccccaggg tngcgctggc    420
cgtccggtcc gtcgggtagt gcccacaacc gcaccaggtt tccccgcccg gccanctcgg    480
ggcgcgcggc aaacctcgcg cnccaagggt gtcntcaanc acctaaaccg ggggtaccgg    540
tggcccataa tggtcntcgc natcaaaaat ccggaacctt acccggcgcn atggttatcc    600
ctggccaacc ggg                                                       613
```

<210> SEQ ID NO 3
<211> LENGTH: 653
<212> TYPE: DNA
<213> ORGANISM: Mycobacterium tuberculosis
<220> FEATURE:
<221> NAME/KEY: modified_base
<222> LOCATION: (1)...(653)
<223> OTHER INFORMATION: n = any nucleotide

<400> SEQUENCE: 3
ccgacagtcg acagaacgtg ttcctcgacg gcaactccaa tctcgtgctg cgcgctaccc 60
gagagggcaa caggtatttc ggtggcctgg tccacggcct gtggcggggt ggcatcggga 120
ccacctggga ggcccggatc aagttcaact gcctggctcc gggcatgtgg cccgcctggt 180
ggttgtccaa tgacgatcct ggtcgcagcg gcgaaatcga cctgatcgag tggtatggca 240
acgggacttg gccgtcngga accaccgtgc acgccaaccc ggacggcacc gcattcgaga 300
cctgcccgat cggtgtggac ggtggttggc acaactggcg cgtcacgtgg aatccgagcg 360
gcatgtactt ctggctggat tacgccgacg gcattgagcc ctacttctcg gttccggcga 420
acggaatcga anactcacga acccatccng cgantggncg ttcaacgacc ccngctacnc 480
ggtgtttccg gtgttgaaac ttgcngttgg cggttctngt ggcgggnatc ccgcgacngg 540
ttcctatccn caggaaaatg ctcntcnant gggtgcccgt cttttaacgc ctcncgctct 600
ttgcccgggg tncttacccg ggttgctccg aaaaagcatt ggaatttttg gtc 653

<210> SEQ ID NO 4
<211> LENGTH: 532
<212> TYPE: DNA
<213> ORGANISM: Mycobacterium tuberculosis
<220> FEATURE:
<221> NAME/KEY: modified_base
<222> LOCATION: (1)...(532)
<223> OTHER INFORMATION: n = any nucleotide

<400> SEQUENCE: 4
gtgtagcggg gctcggtcag aangtagttc agcagcatgc ccgacagcaa ggccaacaat 60
gcggcggggg caacgccgcc cagcaacgcc acaatcagca cgccaataaa aaacaacgcg 120
ctctcgccgc caatgcccat naatcggtcn anccaggcca ccgtnatggc gcaaatcacc 180
gagggcacca ccagcgcggc cagccacaac gcnatatgcc gctcgcgcgg ggagacccgc 240
naccacccgg aggcccggct ggccgcggga tgggtgacat ttnnaacntc natgccgccg 300
gaatcctgga cggtgcgggc ccnatcccct cntcaaacag gcntgcccat cgcnatcgcc 360
gcnaatntgc cnacaacaan ctgcnttggc gttcatctcg cgggcaaaat ccagcagcgc 420
ggtgggcatt cntccccaac cacggttntg catggtcgca ccgaggcttg tcccagctcg 480
cgnaacctgc ccaactgcgg cgcgnaacac ccccgccagg ccgtccccac gg 532

<210> SEQ ID NO 5
<211> LENGTH: 649
<212> TYPE: DNA
<213> ORGANISM: Mycobacterium tuberculosis
<220> FEATURE:
<221> NAME/KEY: modified_base
<222> LOCATION: (1)...(649)
<223> OTHER INFORMATION: n = any nucleotide

<400> SEQUENCE: 5
aattcggcac catgtgagtc ctctcgattc ttgtgcaccg gcatcgcagc gcatcagata 60

-continued

| | |
|---|---|
| gcccagcagg atggtagttg ccggggccccc caggaacacg accgtgacgt tgctcttcgc | 120 |
| cgatctttgc gcgatcttta cgccctaccg gtggatgatt gagcatgtga ccaccaagcg | 180 |
| cgggcagctg cggatctatc tgggcgcggc ccccggcgtg gcaaaaacct acgccatgct | 240 |
| cggcgangcg caccgcangc tggagcgcgg caccgacgtg gtcgccgcgg tcgtcgagac | 300 |
| acacggacgc nacaagaccg cgaaactgct cgagggcatc gagatgatcc cgccgcgcta | 360 |
| cgtcnaatat cggggtgcca ggtttcccga actcgatgtg gaagcagtac tgcgacgtcn | 420 |
| cctcaggtgg tgctggtggg acgaactcgc ccacaccaac acacctggca gcaagaaccc | 480 |
| caagcgctgg caggacttca ngaaatctcg acgccggcat cacggtgatc tcgacggtca | 540 |
| catccaagca atttggaagg gcttaacnat ttcntggaac aatcncggnc tcaaccanaa | 600 |
| ggaaaaaatc cccacnanat ctccgcncgg gccaatcagt caactggtc | 649 |

<210> SEQ ID NO 6
<211> LENGTH: 257
<212> TYPE: DNA
<213> ORGANISM: Mycobacterium tuberculosis
<220> FEATURE:
<221> NAME/KEY: modified_base
<222> LOCATION: (1)...(257)
<223> OTHER INFORMATION: n = any nucleotide

<400> SEQUENCE: 6

| | |
|---|---|
| gcggccgacc ggcatccgca ctgtgcntgg accgtcatca tcgacaattc ctatcgcaag | 60 |
| gctgagggta ttccggcgct ggacgcggtc cgtgaaacca aagctgccac ctgggaatta | 120 |
| nacaacntca atccntctga caacgggctg gtggactatt cgggtccgct ggtgtccgac | 180 |
| ctggacttcg gggcgttctc gcattccgca ctggtgcgga tggccnatna ggtctgcctg | 240 |
| caaatgcacc tgctgaa | 257 |

<210> SEQ ID NO 7
<211> LENGTH: 356
<212> TYPE: DNA
<213> ORGANISM: Mycobacterium tuberculosis

<400> SEQUENCE: 7

| | |
|---|---|
| cggtgcgtgc cgagcagatg gcgatatcag cgagctgctc caccgtcggg ttcgggatga | 60 |
| tcgcgcagtc gccgtacgcc agtacccgat ccggcagaca catcaggaaa atgctggaca | 120 |
| cggtggatat gcccggaacg gtcttgatga tctccagcgc cggacgaacg gtgtgcgccg | 180 |
| tggtgtgagc agcacccgat accatgccgt cggcatgaca gttgtgcacc agcatggtgc | 240 |
| cgaaatatgt ggcatcgttc atgatttcgc gggcatgctc cacggtgatt cccttcgcct | 300 |
| tacgcaactg cgcatactgg tcggcgaatt gatcgtgcag ttcgcttgcg catggc | 356 |

<210> SEQ ID NO 8
<211> LENGTH: 644
<212> TYPE: DNA
<213> ORGANISM: Mycobacterium tuberculosis
<220> FEATURE:
<221> NAME/KEY: modified_base
<222> LOCATION: (1)...(644)
<223> OTHER INFORMATION: n = any nucleotide

<400> SEQUENCE: 8

| | |
|---|---|
| gccngtggcc gtaacgcccc cgttgcagac tcggcgcaac gctaaaactg ctgctgctgt | 60 |
| gctttgccgc cgtaatcact tttgccgcac tgctggtcnt gcaggccaat caaaaccagg | 120 |
| gggtgccctg gnacttnact acctacggac tggccttcct nacccctgttc gnatccgcgc | 180 |

```
atctggccat ccggcgcttc gccccctaca ctnacccgct gttgctcccg gtggtggcac      240
tgctcaacgn acttggcctg gtaatnatcc accgcctcna tctgntgnac aacaanatcg      300
gcaancatcg gcacccagcg caaaccagca aatgctgtga acnctggtgg gcnttacctg      360
ccttcgcgct cgtggtgacc ttcctcaagg accaccnacg gctcccacgc tacggctaca      420
tttgcgggct cgcggngtct ggttttcttg gcantnsccg cgctgctccg gcagcactgt      480
ccnaaacaaa aacggcncca aaatctggga tccggttgcc cggctttctc aaattcaacc      540
cgccaaaatt ttcaaaaaat tctgctgctn atctncttn cggggggtac tgggtggcca      600
aacgcgggct tgttcaccag cgccggnaaa acatttgctc ggaa                      644
```

<210> SEQ ID NO 9
<211> LENGTH: 508
<212> TYPE: DNA
<213> ORGANISM: Mycobacterium tuberculosis
<220> FEATURE:
<221> NAME/KEY: modified_base
<222> LOCATION: (1)...(508)
<223> OTHER INFORMATION: n = any nucleotide

<400> SEQUENCE: 9

```
caccaaccca agctcttcgc cgaacgcggc gatnatgaaa tcggtggatg ccgcgggcac       60
ggtgtcgggt tgaccattac cgagcccggt gccgaagata ccgcctgtag cgaagctgaa      120
aagcgactgc acgatctgat atccggtgcc gtctggatct cgaacggat ccagccaggt      180 ctgtacgcgg agccggacgt gctcaaaaat gaagtacgcc accaaggttc ctgccgcgaa      240
cagagtcagg ccgatgacga ccaactgaac cgctgggtgg cgaggtaaac caccaccaga      300
aacgatgtgt acagcagcag cgaaagcgcc gaggtctttc tcgaagacca tcacacccac      360
cgagatgacc aggctgccaa cagtggcgcg aggtctcncg ggcgcggcag ggtcattccg      420
aacaaatgtt tgccggcgct ggtgaacagg ccgcgtttgg gcaccagtac cgccnaaaan      480
aanatcagca ncagaatctt tgaaaatt                                         508
```

<210> SEQ ID NO 10
<211> LENGTH: 714
<212> TYPE: DNA
<213> ORGANISM: Mycobacterium tuberculosis
<220> FEATURE:
<221> NAME/KEY: modified_base
<222> LOCATION: (1)...(714)
<223> OTHER INFORMATION: n = any nucleotide

<400> SEQUENCE: 10

```
tcgggtgacc agtcgcgccc gttccagggt caccaggccg cggtcggtca tcgctgtnac       60
ntcntcaacc agggnagcgn attttcnatt caatntcaac ggcggcaacg ggtcaccggg      120
cgggtcctcg nacaggctca ncnattgatc gcancnaaac tcntgctttg gcccnaaact      180
ggtggtaccg cgcagcatca cnctggtcgc nactttatgg gagccnaaca natccagcat      240
cgcatcggcc aaaaacctcc ccgccccgcc nacagcgcnt tgccgctccc naaatacncg      300
gncagctnca ggcattgcnc gttcatatct ggggcaatcc actnaccgan tagcgccgcg      360
gctaaaccna gcacaacgct aacaaacaat attggccaat gccnaaacca tctggcggtc      420
ctctcccaac cgttgggttt ctancatcca ggtgnaaaag gtggtgtagg cccaaaaaaa      480
cccgtgccgn gcagtaaggc tgcttctttc ggcaacgcca ggccggccan aaaccccagc      540
agcgcggctc cggtgattnc cccgtcagtg tgccgtaggg naaattccgg gccaccgggg      600
```

```
ggccccgagc gatcgaccan aaaacncccc cggacccaat cccccaata acntcacccc    660 tatccaaatt gccccngtcn gggccgtcaa ggccnntcat cggcgtttcc gccc         714
```

<210> SEQ ID NO 11
<211> LENGTH: 652
<212> TYPE: DNA
<213> ORGANISM: Mycobacterium tuberculosis
<220> FEATURE:
<221> NAME/KEY: modified_base
<222> LOCATION: (1)...(652)
<223> OTHER INFORMATION: n = any nucleotide

<400> SEQUENCE: 11

```
cgacggccac cacctgattg gcggcgagta cctccagcgc cgatacccat gccggttccg    60
aaaggccatg ggtgtcacgg ccgatgaaca gcggcccggt ggtcccctgg gcggcgcggt   120
attcgacgat agcctgggtg atggccagaa tatgtanttc gttgaacgtt ccggtcaggg   180
ctgagccccg gtgccctgag gtgccgaaan cnacctgttg agcgangtcg tcgggatcgg   240
gttcgatcga gtagtacgca gtcaccagat ggggcaggtc gacgaggtct tcgggctggg   300
ccggttgacc ggctcgtggg ttggccacca tggctaccaa ttctgcccac aggccctaca   360
gtgcgaagcg cagcattagc acaccgagag ggatcgacca gtgccaaacc acgattatcg   420
cgagttggct gcggttttcn ccggcggaac gttgggtgcg ctggcccgaa caacgctgaa   480
cgcactcgcc atccccgacc canccggtg ggcatnggcg aagttcacgg tcaaacgtcg    540
tcngcgcctt cctggtgggt ttttcnccac ccggctgctt ggaacaatgc ccctgtcaat   600
tttccacgcc cattgctccg ccccngattg tgcggggaa tgacactttc tc            652
```

<210> SEQ ID NO 12
<211> LENGTH: 536
<212> TYPE: DNA
<213> ORGANISM: Mycobacterium tuberculosis
<220> FEATURE:
<221> NAME/KEY: modified_base
<222> LOCATION: (1)...(536)
<223> OTHER INFORMATION: n = any nucleotide

<400> SEQUENCE: 12

```
agtcatttgg ggatccaacc acaggctccc gccgccggtt gatttgccga acttggtgcc    60
gtcggcagcg gtcaccaagg ggacggtaag cgcatgcacg gtggcaccga gcttctggcg   120
caccaaccgg acgccggcaa tgatgttgcc ccactgatct gcaccaccga tctgcancgt   180
gcagccgtgg cgccggtgca atncgacnta ttcgttggcc tgcagcaaca ggtanctgaa   240
ttcggtgtaa nagatccct cccccgccag acgccgccgg gatggtgtcg cgggccacca   300
ncacgttnac cnagaagtgc ttgccgatat cacgtanaaa cncgatagcc gatagttgaa   360
ccggtccatt ccaggttgtt ctcnacaatc gcgcccattg gtgagtcntc naactcaacn   420
aancnctcca cctgcccacg ngatccgttc ggnccattcg gcgaaggtnt cggcctcgtt   480
naaactgcgc tcgccgacgt cacntggatc accgatcatg ccggtggccc ccccgg       536
```

<210> SEQ ID NO 13
<211> LENGTH: 601
<212> TYPE: DNA
<213> ORGANISM: Mycobacterium tuberculosis
<220> FEATURE:
<221> NAME/KEY: modified_base
<222> LOCATION: (1)...(601)
<223> OTHER INFORMATION: n = any nucleotide

<400> SEQUENCE: 13

-continued

```
gcgccgaagc acagcgcggg ccgatgacgg tgtacgccgg cttcgatccc accgcgccta     60
gcctgcatgc cggacatttg gtgccgctgc tgacgttgcg gcgctttcag cgcgccggtc    120
atcgccccat cgtgctcgcc ggcggggcca ccggcatgat cggtgatcca cgtgacgtcg    180
gcgagcgcag tctcaacgag gccgacaccg tcgccgaatg gaccgaacgg atccgtgggc    240
agctggagcg cttcgtcgac ttcgacgact caccaatggg cgcgatcgtc gagaacaacc    300
tggaatggac cggctcacta tcggctatcg agtttctacg tgatatcggc aagcacttct    360
cggtcaacgt gatgctggcc cgcgacacca tccggcggcg tctggcgggg gaagggatct    420
cttacaccga attcagctac tgttgctgca ggccaacgac tacntcgaat tgcaccggcg    480
ccacgggctg cnccttgcan atcggtggtg caaatcatgg gggaactcat tgcccggntt    540
ccggttgggt gcgccaaaaa ctcggtgcca ccgtgcatgc gctttaccgt ccccttggtg    600
a                                                                     601
```

<210> SEQ ID NO 14
<211> LENGTH: 368
<212> TYPE: DNA
<213> ORGANISM: Mycobacterium tuberculosis

<400> SEQUENCE: 14

```
gcaactacgg cggtatcggt gcgggtggcg caaactcgtc ggcggcggcc aaccgctgct     60
gcgacaccag aagatgactc gacacgcccc gagcggtcgt cggtcgcgcc gggccatccc    120
gggagcatct tgctaccgct tccggaagtg tctttgcggg ggcgccgacc gccctcaggg    180
tcgcctgacg agcgctgtgc ggacccaggc agcaaaggag ctctcggcga atctccgttg    240
gctgctggtt gcccggagtc gccgcatccg cccgacacgg tcatcctgat ctgctcgccg    300
aacacgtggg cgacggacca acgcgcgtgt tttcatcgga tattctgcgg ataacctgtg    360
aaatccgt                                                             368
```

<210> SEQ ID NO 15
<211> LENGTH: 385
<212> TYPE: DNA
<213> ORGANISM: Mycobacterium tuberculosis
<220> FEATURE:
<221> NAME/KEY: modified_base
<222> LOCATION: (1)...(385)
<223> OTHER INFORMATION: n = any nucleotide

<400> SEQUENCE: 15

```
tgtaatgccg cgcaaatcgc cttgcagcac aacatatgtn gagaggccct tcggcaacca     60
cgcttttcgg cagcggtaat ggcggtnttc attgggtcgg gatcntcttc gggtgtcggg    120
tcggccanta catcggcgcc cagcccggcc gccgcagccg ccgcggcttc ntcgggggtg    180
ataacantna tcaancgcat tgaaccgaca cccgccgcgg cggtcaacnt gtcaacaaag    240
catggccagc accactttct cgcaagtctg cnccaaaaaa caccggggcc agcctggttt    300
tggccgcggc caaccncttn acgggcaata atcaagccna tatcccgtcn tccggtgtgc    360
cgctcatnaa ttcatccagc cagcg                                          385
```

<210> SEQ ID NO 16
<211> LENGTH: 489
<212> TYPE: DNA
<213> ORGANISM: Mycobacterium tuberculosis
<220> FEATURE:
<221> NAME/KEY: modified_base
<222> LOCATION: (1)...(489)

<223> OTHER INFORMATION: n = any nucleotide

<400> SEQUENCE: 16

```
caccaaggat cccggctatt cctggacgcc gatcatcttg gccgacggcg cccaccacac      60
caatgccacg tactacaacg acgtgcgcgt gccggtcgac atgctggtcg aaaggagaa     120
cgacgctggc ggctgatcac cacccaactc aacaacgaac gggtaatgct cggcccggcc    180
gggcggttcg ccagcatcta cgaacgggtg cacgcgtggg cgtccgtgcc gggtggcaac    240
ngcgtgaccc gatcgaccac nacaactcna gcgggctctt ggtgagattc gtgcgatctg    300
gcggatcaac ganttgctca actggcaggt ancgtccgcc ggtgaggaca tcaacatggc    360
cgatgccgcg gncacgaaag tctttggcac cgaacgtgtt cancgttgcc ggccggctcg    420
cccaangaaa tcgttggcaa ttacggaacc cgccgaaccc aacnccgccn aacttctgcg    480
ctngctgga                                                            489
```

<210> SEQ ID NO 17
<211> LENGTH: 453
<212> TYPE: DNA
<213> ORGANISM: Mycobacterium tuberculosis

<400> SEQUENCE: 17

```
gtcccaaggc ctgatcgaat ccaccaacac caagatccgc ctactgaccc ggatcgcgtt     60
cggattccgc tcaccacaag ccctcatcgc cctagccatg ctcaccctcg ccggccaccg    120
ccccacccctg ccaggccgac acaaccaccc acagatcagt cagtagagcc caattcgtac  180
cgaatttggg ggcttttacg tctgctcgcg ctacccagct agaccgggat caggccgtgc    240
ttgcggccca cccgccacca cagctgcttg tccgcagcag gtgcatcgac ttgcgcaaca    300
gcagccgggt ctcatgcggg tcgatgacgg catcgatgaa cccgcgctcg gcggcgatcc    360
acgggatcgc catgttgagg ttgtaattct cgacgaagct cttccggatc gcttgcgcct    420
ccggcgcatt cgggtccggg aaacgcttca tca                                 453
```

<210> SEQ ID NO 18
<211> LENGTH: 504
<212> TYPE: DNA
<213> ORGANISM: Mycobacterium tuberculosis
<220> FEATURE:
<221> NAME/KEY: modified_base
<222> LOCATION: (1)...(504)
<223> OTHER INFORMATION: n = any nucleotide

<400> SEQUENCE: 18

```
cggcgccagc cacaacggaa atgtgggact tgtcgatgct gggtatcgtg cccggcatcc     60
gggtggcagc gcccagagac gccacccggt tgcgtgaana actcggcgag gcgctcgacg    120
tcgacgacgg cccgacggcg ttacggttcc caaaggtga tgtgggagaa gatatntcgg    180
ctttggagcg gcgtggaggc gtggatgtgc tggcggcgcc cgccgatggt ttgaaccacg    240
acgtcctgtn ggtggccatc ggcgcgttcg caccgatggc gttggcggtg gccaagcgct    300
gcacaaccag gggatcggtg tgacggtgat cgacccgcgc tgggtgttgc cggtgtctga    360
cngtgtgcgc gaactggcgg tgcagcacaa gctgctcctc acgctanaag acaacgggt    420
caacggtggg gcggggtcna ccggtgtcng ccgcnctgcg gcgcccggaa atcaacctgc    480
ctgccgcgat ttcgggttnc cgca                                           504
```

<210> SEQ ID NO 19
<211> LENGTH: 300

```
<212> TYPE: DNA
<213> ORGANISM: Mycobacterium tuberculosis
<220> FEATURE:
<221> NAME/KEY: modified_base
<222> LOCATION: (1)...(300)
<223> OTHER INFORMATION: n = any nucleotide

<400> SEQUENCE: 19
tcggcaatcc atgccgacgg tgcaccgcat cnaaaccact gtcccgcaag gcttgtggcc      60
aatcntcacg caggtcaang gcnaatctcg cngcgcaggg cgcgcggttg ggcaccgtgg     120
ctggcnanca cctccgcttg aaatcaagga ctgcgggcgg tccactcaaa aaccgtggtc     180
cgtcgggccn aggcnnccgg tacnncgcna tnccagcccc gccgccagga taaccacctg     240
cccncnccng nggnggggggc ccgaacggaa attactcctc aaaatattgg tgcgggcacc   300

<210> SEQ ID NO 20
<211> LENGTH: 528
<212> TYPE: DNA
<213> ORGANISM: Mycobacterium tuberculosis
<220> FEATURE:
<221> NAME/KEY: modified_base
<222> LOCATION: (1)...(528)
<223> OTHER INFORMATION: n = any nucleotide

<400> SEQUENCE: 20
aattcggcac gagttccgtc atctccaact tgggtgcggt gaccgggttc gccgggctat      60
ccggcttggc cggcatgcan ccggcggnta tcccggcgct accaccgtc gcggcggccc     120 cgccgacatt gccggcggtc gcgatggccc cgaccatggc cgcgccgggc gcggnggttg     180
cgtcagcaac cgccgccggcg tccgcgccgg cngccagcac ggtggccntt ntcnnnccgg     240
caccgccgcc ggcacccggc gccgccgggt tcngctatcc ctacnccatc gctccnccg      300 gcatcgggtt cggctcgggg atgaccgcca gcgccnacnc tcaacncaan gcaccacact    360
cccnatattg ccgccgcggc ngcngcccgc ngcggccnta ctttaacaaa cccgggcgcg    420
gcggcggccc nttgtccccg gccnggatac ggcaacaatt ttatggatat caaactcgac    480
ctcaatcccg actggggccc tccgcccggc gaaaaaccca ttccatcc                  528

<210> SEQ ID NO 21
<211> LENGTH: 198
<212> TYPE: DNA
<213> ORGANISM: Mycobacterium tuberculosis
<220> FEATURE:
<221> NAME/KEY: modified_base
<222> LOCATION: (1)...(198)
<223> OTHER INFORMATION: n = any nucleotide

<400> SEQUENCE: 21
aggatcgact cagngaattg ggtgagtcgg tggccatcgc cgctgctccg cccgacagct      60
actccgtaca cttccacacc gacaacgccg gtgccgccgt gnaagccgga ttggcggtgg    120
ggcnanttag ccggatcgtg atctcggcgc tcggttccgg gaccancgga ttgccggccg    180
gtggctggac ncggggcc                                                   198

<210> SEQ ID NO 22
<211> LENGTH: 492
<212> TYPE: DNA
<213> ORGANISM: Mycobacterium tuberculosis
<220> FEATURE:
<221> NAME/KEY: modified_base
<222> LOCATION: (1)...(492)
<223> OTHER INFORMATION: n = any nucleotide
```

-continued

<400> SEQUENCE: 22

```
ctatgcggtt gcggtccggt gccgccactc cagaggtcca gcaatnaggt cgcntcggga     60
tcaacctctt cgggggcctg ggtgacttta attcccacac cgattaccac aaacggctgc    120
gcaacctcgg ccagggatgc cggctaactt gccaccccgg gccancactt cnttgggcca    180
cttnaggccc gtttcggccg gcgggactgc aatcaggggg gccaccgaat caacaccgcc    240
aaaccccggc caattaacac caaccccncc cttggaccgg gaactncaac acacnccacc    300
cgaacgaacg gatgatntnc cctcgggcan tggccgccaa ccncggcatn acccccccgcc    360
agcggtctga tctcggcaat caacaccacc cgtcaattcg gccccggatg ccncccgggc    420
caacaantcg gntttggtgg aaccggtttg gggcccaaan tcaatttggc gcccccccgga    480
tccaacaccg at                                                        492
```

<210> SEQ ID NO 23
<211> LENGTH: 585
<212> TYPE: DNA
<213> ORGANISM: Mycobacterium tuberculosis
<220> FEATURE:
<221> NAME/KEY: modified_base
<222> LOCATION: (1)...(585)
<223> OTHER INFORMATION: n = any nucleotide

<400> SEQUENCE: 23

```
gtttcgtgcg atcaactccc atggcagggc gctatttacg ctggcgcatc gggcgatggc     60
cggccatgac naanacgact acgtcatcac cgacggcgaa cgggtctgca gcactgccgt    120
cggctggaac ttcggcgacg gccacctgca caacgagcaa ctgatcgcgg cgatgcaaca    180
gcggtgcggc ttccaacccg gtgaggtgcg ggtggtgctg ctcgacgcgc agcccatcca    240
tcggcaaacc caggagtacc ggttggtaca cgcggcgacc ggggagttcg agcgcggcta    300
tgtccgggtg gccgacatgg tgaaccggca gccctgggac gacnacntgc cggtccacgt    360
gctgccgggc tagctgctcg tcanctagcc cgcgcgcacc tcccggggcg ggggngaaca    420
tgtttgcagc gacgcggtca cctcgtcgac attgcgggtc ttcatccgca gtcgggggtg    480
aaccacagcc gctcgggcgg caccgcgcgc aacgcggccg caacgaatcn gccatctctc    540
nncggaaggc acccgttggg aattaatgtn ataaacnccc ggncc                    585
```

<210> SEQ ID NO 24
<211> LENGTH: 223
<212> TYPE: DNA
<213> ORGANISM: Mycobacterium tuberculosis
<220> FEATURE:
<221> NAME/KEY: modified_base
<222> LOCATION: (1)...(223)
<223> OTHER INFORMATION: n = any nucleotide

<400> SEQUENCE: 24

```
gagttctaca gagagtttca ggctgccaga gaaacaactt cgtacacgca aggctggcac     60
cctggtaggc cggcccgcat tcgcaccagg gtgggaacaa gggagggtga tggaacagca    120
cacgctgctg caacgcaagg antcgccgcg cantcccgcg gccccttcgc tcaggcgcct    180
gggtggctca cttcacatca cgcattggga tcccnaggat cta                      223
```

<210> SEQ ID NO 25
<211> LENGTH: 263
<212> TYPE: DNA
<213> ORGANISM: Mycobacterium tuberculosis
<220> FEATURE:
<221> NAME/KEY: modified_base
<222> LOCATION: (1)...(263)
<223> OTHER INFORMATION: n = any nucleotide

<400> SEQUENCE: 25

| aattcngcac | ctggtaacgc | tccgttgcac | cgtcggtgta | ggttacgtcg | accaggacta | 60 |
| ggtcgaggtt | gtgtcgcagg | gcgacnacta | cgcccggctt | gaccgtggcc | agctcgcggt | 120 |
| tgcgtccggc | ataccaacgt | tgccgcggaa | gccaatcgga | ccatgcagc | ttggttgcca | 180 |
| gcgtgtccga | ccgagtcata | ngcgccgctc | ctcctcatcg | cttcgctgtg | catcgtcgct | 240 |
| ggcgcgagtc | atangctcgt | gcc | | | | 263 |

<210> SEQ ID NO 26
<211> LENGTH: 242
<212> TYPE: DNA
<213> ORGANISM: Mycobacterium tuberculosis
<220> FEATURE:
<221> NAME/KEY: modified_base
<222> LOCATION: (1)...(242)
<223> OTHER INFORMATION: n = any nucleotide

<400> SEQUENCE: 26

| tatcctcgac | taccatatct | ccgaagacgc | cntctattcc | gacggcaggc | cggtnacctg | 60 |
| tgacaacctg | gtattggcct | gggcggccca | atccggccgc | tttcccggct | tcnacgctgc | 120 |
| tacgcaggcc | ggctatttca | acntcgccaa | cntcnattgc | acgcgggc | aaaaaaaggc | 180 |
| ccgggtgtcg | ttcancccgg | atcgcagtgt | cgttnaacac | tccagctttt | cnccgcgacg | 240 |
| tc | | | | | | 242 |

<210> SEQ ID NO 27
<211> LENGTH: 551
<212> TYPE: DNA
<213> ORGANISM: Mycobacterium tuberculosis
<220> FEATURE:
<221> NAME/KEY: modified_base
<222> LOCATION: (1)...(551)
<223> OTHER INFORMATION: n = any nucleotide

<400> SEQUENCE: 27

| agtaccccga | tagattgttt | ccgttgccgc | tgtgcaagtc | ataggcatcc | atcgcagacn | 60 |
| atccgctcga | tccgctgccg | gtggccccac | cggtgctcgc | caacaatacg | tcaatctttc | 120 |
| cgtcccgcag | cgcttgcggt | ccgggtgtgt | ccaccgtcac | atccgaaacg | gtgatcccgg | 180 |
| ccggggcgca | ngcgtcggca | atggttccga | tngtggccgc | caaccgancg | ttgggcctgc | 240 |
| cgtaccgatc | cgcacggtca | gcggcgtacc | acccagcgcg | tcgcgagcgg | cggcggggtc | 300 |
| caccggccga | actgacgtgc | ttcggcggcg | ccgtcggcat | cggtgaaggc | atcgtccgtc | 360 |
| gccggggaca | gccgcgaatt | ggcaatcgga | accccggcat | cccgagcgat | cgcctcccgg | 420 |
| ggtacacaca | acgccaagcg | cgcggcgggt | tgcggntttg | cgcnattaaa | cttgttggtg | 480 |
| cgaaaatcac | tgctcgatcc | ngccnacgg | ttattcggtg | cgctngtact | gtcggggtt | 540 |
| acccgggatc | c | | | | | 551 |

<210> SEQ ID NO 28
<211> LENGTH: 101
<212> TYPE: DNA
<213> ORGANISM: Mycobacterium tuberculosis
<220> FEATURE:
<221> NAME/KEY: modified_base
<222> LOCATION: (1)...(101)
<223> OTHER INFORMATION: n = any nucleotide -continued

```
<400> SEQUENCE: 28
tctgatcgtg tctttggtta cacanacggg ctcaggcttt agagatctct tcgcanttaa      60
gggtgtnagg tattcggcgc ttcnttgccg gggtaggggt c                         101

<210> SEQ ID NO 29
<211> LENGTH: 507
<212> TYPE: DNA
<213> ORGANISM: Mycobacterium tuberculosis
<220> FEATURE:
<221> NAME/KEY: modified_base
<222> LOCATION: (1)...(507)
<223> OTHER INFORMATION: n = any nucleotide

<400> SEQUENCE: 29
atcangttgt cgcccagggc gcgtcgtgcg atcgcagccg cggatatccc tggggtgtgc      60
tcgttgcggt caaaancaat accggtgcgc cggatctcaa caatctcgcg ccgtaaacct     120
tcggccacca tgggatccaa acggnaaaan cgcggcctcg gcntcggcnt cttcaaaagc     180
aaccancgcc gcttttccat tcgcggttcc ttcaacggga ancggaacc canggtgaaa     240 ncgcacccag ccngtaaaaa nantccattt ggtcnanaaa ccnaattcnc tnggcgcgca     300
ntancnaaag gtcgaccgtt tccccgtcgg tccccgggca actcnntcaa cggtcggccg     360 naaccccgg ctattttggc tccggtnana cttcccaatc ccagcaaacc tccccattgc     420
gaacggcntg cnaatccaca ctaaccangc cccntcgacc aggccgaaca ccaagcgtca     480
aatctccatt tggccagccc cacccgc                                         507

<210> SEQ ID NO 30
<211> LENGTH: 589
<212> TYPE: DNA
<213> ORGANISM: Mycobacterium tuberculosis
<220> FEATURE:
<221> NAME/KEY: modified_base
<222> LOCATION: (1)...(589)
<223> OTHER INFORMATION: n = any nucleotide

<400> SEQUENCE: 30
cggccatgtg ggaccgcgcc cagtcggcgt acttcgcctc gtcggccgga tccttccagg      60
agccgtagag cgccaagtag atgtcggctt cgatgctata ggccatgtct tgacggggag     120
ggcatggacc ccagttcagc cagaggaagt gcgccggatg cgggggcanc gtgtccanga     180
ttgancggat accggcagc aggtcctcag cggacgccga cgtccacata ttgtccaccg     240
cgtantgatg gtctgacagg tagtgggtca tcgcgacgtc ataccaggca ggcaaatcgg     300
ttggcatata agggactttg accagtgcct gctcgacaac cgggcaggtg ccgaacaggg     360
cgaaggcctg ttcggcctct tcgggcgant cancgaaagc gggcgaagca aggganatga     420
cggggacntc natgcccatg ctcggttcac cgcgggaagc aagggcttgc actcgacccg     480
aaggtcaact tcggcgctta ccgcgccggc ccangttaaa actcctccgc aaggtcnaat     540
gggttaacnt aaacctggtg ccccaggtgg ccggnctcgg atacagntt                 589

<210> SEQ ID NO 31
<211> LENGTH: 260
<212> TYPE: DNA
<213> ORGANISM: Mycobacterium tuberculosis
<220> FEATURE:
<221> NAME/KEY: modified_base
<222> LOCATION: (1)...(260)
<223> OTHER INFORMATION: n = any nucleotide

<400> SEQUENCE: 31
```

```
ttaatcatct tcaccgggct ctantgcggc gcaagcttgt caacagatct cgaattcggc      60
antagcttca tgaccgagca ttcttcggcg ctaaggccga ttacaacaac tatcgccgcg     120
cggccggacc ggccnaccac accgcgccgc caatcatcna ggaactgaaa accaaggcca    180
aaaaccgcgg cctgtggaac ctattcctgt cggccnattc gggattnacc aacctgggat    240
tacgcgccgc tggccgaaat                                                260

<210> SEQ ID NO 32
<211> LENGTH: 240
<212> TYPE: DNA
<213> ORGANISM: Mycobacterium tuberculosis
<220> FEATURE:
<221> NAME/KEY: modified_base
<222> LOCATION: (1)...(240)
<223> OTHER INFORMATION: n = any nucleotide

<400> SEQUENCE: 32
aattcggcac gagccggggg tgtcgatcgg gacnaaggac catcgactgc tgttggtggg      60
cggctgcgtc cgggttggtg cggcccatca cgatgaggat cttgcaccgc gggtccgccg    120
ctcccgacgt ccaccactta cggccgttga tgacgtantc ggcaccgtcc cgggagatgg    180
tggtttcgaa tgttgcgggc gtcgctgctg gccaccgccg gctcggtcat cccccccccc    240

<210> SEQ ID NO 33
<211> LENGTH: 233
<212> TYPE: DNA
<213> ORGANISM: Mycobacterium tuberculosis
<220> FEATURE:
<221> NAME/KEY: modified_base
<222> LOCATION: (1)...(233)
<223> OTHER INFORMATION: n = any nucleotide

<400> SEQUENCE: 33
aattcggcac gagccaggca agcgcagcac atgactggcc gatccgttgg cgaggtctct      60
tgtcatggcg tcgatcacgt gctggtcgtc gggatgtaga cnaggcccat cggccgcgct    120
acgccgccag tcgtanaaag agcagggttg gtcgagccat ttcagcaggg tccaggtttt    180
gagatcgacc agtgcccgca ccgatcgccc ttcccaacag ttgcgcagcc ccc           233

<210> SEQ ID NO 34
<211> LENGTH: 219
<212> TYPE: DNA
<213> ORGANISM: Mycobacterium tuberculosis
<220> FEATURE:
<221> NAME/KEY: modified_base
<222> LOCATION: (1)...(219)
<223> OTHER INFORMATION: n = any nucleotide

<400> SEQUENCE: 34
cggcaagagt cgaatgtttc caagactacc tggagcgggt nttcttgccg ggtcgggtct      60
ttgcctctcc ggcggatttc aatacccatt tgcaggcctg gntggtgcgg gccaatcacc    120
gccagcaccn attgctggga tntcnaccgg canatcgcat cnaggccnat accgcagcna    180
tgctnacatt gccgccggtc gggcccagca tcgggtggc                           219

<210> SEQ ID NO 35
<211> LENGTH: 186
<212> TYPE: DNA
<213> ORGANISM: Mycobacterium tuberculosis
<220> FEATURE:
<221> NAME/KEY: modified_base
<222> LOCATION: (1)...(186)
```

-continued

<223> OTHER INFORMATION: n = any nucleotide

<400> SEQUENCE: 35

```
aatgtttcca agactacctg gagcgggtnt tcttgccggg tcgggtcttt gcctctccgg      60
cggatttcaa tacccatttg caggcctggn tggtgcgggc caatcaccgc cagcaccnat    120
tgctgggatn tcnaccggca natcgcatcn aggccnatac cgcagcnatg ctnacattgc    180
cgccgg                                                                186
```

<210> SEQ ID NO 36
<211> LENGTH: 207
<212> TYPE: DNA
<213> ORGANISM: Mycobacterium tuberculosis
<220> FEATURE:
<221> NAME/KEY: modified_base
<222> LOCATION: (1)...(207)
<223> OTHER INFORMATION: n = any nucleotide

<400> SEQUENCE: 36

```
cggcangagc tgatcaaccg gatcggtgtc aacgcacagt ccgacttcgg catcttgcgg      60
atcggtatcg gcggtggtca naccattnac ttgaacttct tgttgtcggc agcnatcaac    120
tttttcctga tcgcnttcgc ggtgtacttc ctantcntgc tgccctacaa cacactacgc    180
aanaaggggg aggtcaagca gccgggc                                         207
```

<210> SEQ ID NO 37
<211> LENGTH: 238
<212> TYPE: DNA
<213> ORGANISM: Mycobacterium tuberculosis

<400> SEQUENCE: 37

```
aattcggacc tgagggtcgg tcagccggtg ctggcgatcg ggtcgccgct cggtttggag      60
ggcaccgtga ccacggggta tcgtcagcgc tctcaaccgt ccagtgtcga cgaccggcga    120
ggccggcaac cagaacaccg tgctggacgc cattcagacc gacgccgcga tcaaccccgg    180
taactccggg ggcgcgctgg tgaacatgaa cgctcaactc gtcggagtca accccccg      238
```

<210> SEQ ID NO 38
<211> LENGTH: 213
<212> TYPE: DNA
<213> ORGANISM: Mycobacterium tuberculosis
<220> FEATURE:
<221> NAME/KEY: modified_base
<222> LOCATION: (1)...(213)
<223> OTHER INFORMATION: n = any nucleotide

<400> SEQUENCE: 38

```
gatctcgaat tcggcaagag cctgtagttg ggttcncatt gcaccgtcgc cgaccatcac      60
tcgctgcnac aaacgtcaa gcaaatcggt gtcgtaaagg tgcttgtcgg ccgcantcac     120
atggcaagga tantcggcct atgaaatttc ctcantcgtt nacagcgctc tgccaggtac    180
cgcnacntcg catcggtcac agctgccaca aaa                                  213
```

<210> SEQ ID NO 39
<211> LENGTH: 261
<212> TYPE: DNA
<213> ORGANISM: Mycobacterium tuberculosis
<220> FEATURE:
<221> NAME/KEY: modified_base
<222> LOCATION: (1)...(261)
<223> OTHER INFORMATION: n = any nucleotide

<400> SEQUENCE: 39

```
tataatcatc attcactggg ctctatgcgg ccgcancttg tcgacagatc tcnaattcgg    60
cacgagaatg tcgttatcgg tgtgtccggg ggattggact cnacgcacgc gctgatcgtc   120
gcnacccatg ccatggaccg cnagggccgg ccgcgcagcn acattctggc ntttgctttg   180
cccggattcg ccaccgggga gcacactaan aacaacgcna tcaanctggc acntgcnctg   240
ggggttacct tctccgaaat c                                              261
```

<210> SEQ ID NO 40
<211> LENGTH: 233
<212> TYPE: DNA
<213> ORGANISM: Mycobacterium tuberculosis
<220> FEATURE:
<221> NAME/KEY: modified_base
<222> LOCATION: (1)...(233)
<223> OTHER INFORMATION: n = any nucleotide

<400> SEQUENCE: 40

```
aattcngcac caggtgtgca gcatcaaccg agcggtgtcg ccgatatcga tttcggagaa    60
ngtaaccccc agcgcacgtg ccagcttgat cgcgttgttc ttagtgtgct ccccggtggc   120
gaatccgggc aacgcaaacg ccagaatgtc gctgcgcggc cggccctcgc ggtccatggc   180
atgggtcgcg acgatcagcg cgtgcgtcga gtccaatccc ccggacaccc ccc          233
```

<210> SEQ ID NO 41
<211> LENGTH: 475
<212> TYPE: DNA
<213> ORGANISM: Mycobacterium tuberculosis
<220> FEATURE:
<221> NAME/KEY: modified_base
<222> LOCATION: (1)...(475)
<223> OTHER INFORMATION: n = any nucleotide

<400> SEQUENCE: 41

```
ggtaccctgg tgtcgcttcg cccggaagaa tacttctacc ccgacatgcc caanaactac    60
caaatctcac agtacgacaa agccgatcgc catcaacggc tacctggacg cgcctttgga   120
agacggcacc acttggcggg tggagattga gcagctcca tggaanaaga cccggcaagc   180
tcacccacat cggcngcgan aacgggccgg atccacggtg ccaccgggtt cgctgatcna   240
ctacnaccgt gccggcgtgc cgctcatcga natngtcacc aaacccatcg tgggcccggt   300
gcccgggccc gcaaatcgcc cggtcctatn tgacggcttt gcgggatctg ctgcgcgcat   360
taaatttnct gatntccgga tggaccaggg ttcgatgcgc tgtgacccca acgtntcgct   420
naacccggcc gggacaacga atncggcccc ggaccgaaac caanaacnnc aactc        475
```

<210> SEQ ID NO 42
<211> LENGTH: 577
<212> TYPE: DNA
<213> ORGANISM: Mycobacterium tuberculosis
<220> FEATURE:
<221> NAME/KEY: modified_base
<222> LOCATION: (1)...(577)
<223> OTHER INFORMATION: n = any nucleotide

<400> SEQUENCE: 42

```
agccgccctc ttggtggtca gaccgaacct gcgcatgacc tcggcggcaa gttcgtcatc    60
gatgtcgatg ttggtgcgcg acatacacca acgatacaca tgcgaagttt gtcggcacgg   120
tcgcgccgac cctcgctaca gcagatacgc gttagccggc gacccggttc caacgcctcg   180
acgtgaatgt cggtcgccgc atccgggcca cagacgtcta natccgcggn cgatccngct   240
```

-continued

| | |
|---|---|
| cgataccacc agnnctcacc ggtctccggg tgttgccttg actactcaac aagtgatgtc | 300 |
| tcgttgggtc cgancacgtc tcnanaaacg gcgcacgcac gggctcctgc gggaagtcaa | 360 |
| caaggaaata gtgcttgang ccangtggaa cagcgancgc tccaacacct cccgtaacgg | 420 |
| gacacntcgt tgttgccgcc gaaatcaggc ccaccacggt ggaccnggct cnatgtcgct | 480 |
| tncaacagaa cgggnaacga cagggcaccg gccggttcgg gcaataatcc ctcnttctga | 540 |
| tacanatcaa cancgccgtg caaaccggan cctcgtc | 577 |

<210> SEQ ID NO 43
<211> LENGTH: 239
<212> TYPE: DNA
<213> ORGANISM: Mycobacterium tuberculosis
<220> FEATURE:
<221> NAME/KEY: modified_base
<222> LOCATION: (1)...(239)
<223> OTHER INFORMATION: n = any nucleotide

<400> SEQUENCE: 43

| | |
|---|---|
| ggtttaatca atcattcacc gggctctant gcggcgcaag cttgtnnaca gactcgaatt | 60 |
| cggcaagagg gagccaactg attgtcgttc actcctaaaa gctacgccag atttctggaa | 120 |
| aattcggcca aaggcggtcg gttcgccggc tttaggcccc ggnaccggga tccgtgntct | 180 |
| gctcgggcgc agccgcnact tcttcaatcc ggtactggcg ggcggccgca accggcacc | 239 |

<210> SEQ ID NO 44
<211> LENGTH: 231
<212> TYPE: DNA
<213> ORGANISM: Mycobacterium tuberculosis
<220> FEATURE:
<221> NAME/KEY: modified_base
<222> LOCATION: (1)...(231)
<223> OTHER INFORMATION: n = any nucleotide

<400> SEQUENCE: 44

| | |
|---|---|
| aattcggcac gaggtatcta ccgctatcac gcggccaccg agcaacgcac caacaaggcg | 60 |
| cagatcctgg cctccggggt agcgatgccc gcggcgctgc gggcagcaca gatgctggcc | 120 |
| gccgagtggg atgtcgccgc cgacgtgtgg tcggtgacca gttggggcga gctaaaccgc | 180 |
| gacggggtgn gccatcgaga ccgagaagct ccgccacccc gatcggccgg c | 231 |

<210> SEQ ID NO 45
<211> LENGTH: 440
<212> TYPE: DNA
<213> ORGANISM: Mycobacterium tuberculosis
<220> FEATURE:
<221> NAME/KEY: modified_base
<222> LOCATION: (1)...(440)
<223> OTHER INFORMATION: n = any nucleotide

<400> SEQUENCE: 45

| | |
|---|---|
| cggcacgagt acccacagcc gtgttaggtg ctggtggtcc gaaccggcgc tggacaatat | 60 |
| cggcgggacg ggctgtggcc ggatcagcna tcgtggctgg caancggtca caatcnatct | 120 |
| gcgcgggcat ggcnaatccn actggtcgan cgaaggcctg gtgccgaatt cggatccnat | 180 |
| atcgccatgg ccttgtcgtc gtcgtcggta cccagatctt ggtatnctat agtgtcccta | 240 |
| aatgcnnatc tgggctgttc atntgccggc gtncgaattt agcagcaggc ggtttctttc | 300 |
| ataccanaaa ccgcntggcn ccagaccaga agaatgatga taatgatggt gcatatcaga | 360 |
| accaccgcca ccccaattcg atccggtacc agcaccacca gcgtgaggt gcggaacttc | 420 |
| tacaacctca aagccataac | 440 |

<210> SEQ ID NO 46
<211> LENGTH: 654
<212> TYPE: DNA
<213> ORGANISM: Mycobacterium tuberculosis
<220> FEATURE:
<221> NAME/KEY: modified_base
<222> LOCATION: (1)...(654)
<223> OTHER INFORMATION: n = any nucleotide

<400> SEQUENCE: 46

| | | | | | |
|---|---|---|---|---|---|
| cggcacgagc | ggtattcggt | tgaccagacc | ggtctgtcgc | tcgccatgcc | caccggtggc | 60 |
| atggcaantt | ctattccaac | tggcaccggc | cggcggtcgg | caacggcggg | atatggccca | 120 |
| aaagctggcc | nactggctgg | cggcaaatga | ggggatcatc | ccnagtggaa | atggcgtggt | 180 |
| tgccggatcc | gcgtcattga | tccgggggcc | nccgaccgat | ccggcntggg | cccacagcna | 240 |
| ccaacggtca | atgccgcnaa | actggtggcc | aaacagcacc | ccgtatctgg | gcntatncgg | 300 |
| gcaacggcac | cccncggcgg | aattnaacgg | caataggcna | caggctttgc | aaancaanta | 360 |
| ccaagcggcg | caacggcggt | tcacttcccg | gatggcnaaa | cccacacctg | ggcgtatggc | 420 |
| gttgcgccat | tgcaggccat | gctgcctgat | ctgcaccggg | tgctgggcna | cggtcaacgg | 480 |
| cctcggcggg | gggccnaggc | cccnaaaaac | ncagcccgc | anccccaaac | ctgttaaata | 540 |
| ccgcnacaaa | cggganaatt | gccncnaaac | caanaactaa | aggcccggca | aaaaancggc | 600 |
| tcttatcaac | ccnccccgg | atttgggttc | aaacatgaac | tcccccaat | cccc | 654 |

<210> SEQ ID NO 47
<211> LENGTH: 663
<212> TYPE: DNA
<213> ORGANISM: Mycobacterium tuberculosis
<220> FEATURE:
<221> NAME/KEY: modified_base
<222> LOCATION: (1)...(663)
<223> OTHER INFORMATION: n = any nucleotide

<400> SEQUENCE: 47

| | | | | | |
|---|---|---|---|---|---|
| aattcggcac | gagtcggcat | agtggcgcaa | cgcttggtac | accatcaccg | gacccaaatc | 60 |
| cgaaccaccg | atgccgatgt | tgacgacggt | gctgatccgc | tttccagttg | ctccggtcca | 120 |
| ctcgccgctg | cgcaggcgt | cggtgaangc | gcccatcgcg | tcgagcacgg | catgtacgtc | 180 |
| ggtgacgact | cttggccgtc | gacnacaatt | cggcgtctcg | gggcancgca | ncgcggtgtg | 240 |
| cacaccctcg | atctcnnaag | ttttgaaatg | cacaccgggn | aacatctggt | cncgaagctc | 300 |
| ttcnaagtgg | ggcgtccggg | ccagatcgat | cagcaacgcc | gcgtctcgcc | ggtgaaccgg | 360 |
| tgtttgctgt | tattcaatgt | tananatccc | gacctnaacg | gtganctccc | gggcgcgacc | 420 |
| ggatcgtcgg | cgaagaactg | gcgaananng | gtgtttccat | ctgatcgtga | tgtctgcgca | 480 |
| gggggtccca | tgccgggggtt | accggtnatn | tcngggaatt | ggccccgaag | gtcatggttc | 540 |
| gaccttantc | cgtggaatgg | ggtcaatcaa | aaccgctgtc | ttccccaacc | tttantttc | 600 |
| gttctcgggg | gactccccgt | ttgtcccgtn | tctacagggt | ccggcaaagc | ggggctgcgc | 660 |
| ttt | | | | | | 663 |

<210> SEQ ID NO 48
<211> LENGTH: 607
<212> TYPE: DNA
<213> ORGANISM: Mycobacterium tuberculosis
<220> FEATURE:
<221> NAME/KEY: modified_base
<222> LOCATION: (1)...(607)

<223> OTHER INFORMATION: n = any nucleotide

<400> SEQUENCE: 48

```
ggagggcgca natcgcgccg gtcaccgcgc tgtaaatgtc ggattgggtc aaggtcacca      60
cccgggcggc naaacntcna cgcnttnaat ccgtgctcgg cntaaaggat catcnactgc     120
tcnaacgccn acacnacggc ggtttcgggt acctccccna agcacatgtg caggaanttc     180
tgcgcataac cnacccgct gtgcggtgcn atcggggca accgcgtcgg cgcccatgtc      240
aatcgccacg atcgtcggca acaccgccat cattgcgcat cgccttggcc cggttggccg     300
cgggggtctt cctcgtccgg gtcctcggca ccganataac tnatcgcggt gcgcaccacn     360
tccatcgggt ggcagttgtc cggcagcttg gccagcaatg acagcatcaa agcggtccac     420
cnacggctgg ctcgttcgcg ctggctgaac aaccccagct cggcatcggt gggcactcac     480
cacnccnana gcanggaagg caaactgctc gaaatgcacg gggctgccaa atcctggacc     540
ggaatatccc ggtnggtcaa caaattggtc tgcggcnccn cttggaaaat gggggtggtn     600
tccacca                                                              607
```

<210> SEQ ID NO 49
<211> LENGTH: 676
<212> TYPE: DNA
<213> ORGANISM: Mycobacterium tuberculosis
<220> FEATURE:
<221> NAME/KEY: modified_base
<222> LOCATION: (1)...(676)
<223> OTHER INFORMATION: n = any nucleotide

<400> SEQUENCE: 49

```
aattcggcgc cgactccgac gaggttcgcc actatatcat cgactgcgcg ctgcgatgga      60
tgcgcgactt ccacgccgac ggcttgcggt tggacgccgt gcatgcactg gtggacacca     120
ccgccgtgca tgtcctcgag gagcttgcca acgcgacccg cttcgacagg tgtgttgcgg     180
tgtttctcaa cggtgaagcc attaccgcac cggacgcccg tggtgagcga gtattcgacn     240
attcattcct gttgtgcttc aacgccatg accacgacgt gganttcgtg atgccgcatg      300
acggctatgc gcagcagtgg accggaganc tggataccaa cgatcccgtc ggtgacatcg     360
acctgacggt aaccgccact gacacgtttt cggtacctgc gcgctcgctg ctggtcctgc     420
gtaagacgtt tgaaatatgg catttccggt tatttccact taccgggtgc anatgcgcgg     480
tcggtcnaac ggattcgggt ctcgccgatc tcganagcgg tgccgtgggt gggctgaacg     540
tgttggtcna tccgcgggtg ctggacaaag cgccggtgat tccccaggaa tctttcaatg     600
aacgggcgc tcgcggcggg caggtccgtc ctgccacaaa attcaataac gcgccccccg      660
tttaataacg gccgac                                                    676
```

<210> SEQ ID NO 50
<211> LENGTH: 364
<212> TYPE: DNA
<213> ORGANISM: Mycobacterium tuberculosis
<220> FEATURE:
<221> NAME/KEY: modified_base
<222> LOCATION: (1)...(364)
<223> OTHER INFORMATION: n = any nucleotide

<400> SEQUENCE: 50

```
cctgcgctgg aagccgttgc cgcactggct gattcgttgc gccgcgatgt cgtcggcaac      60
aaaggtgacc tttgtggtca accgtaacat caacttcacc aacatctgct acaccggttg     120
ccggttctgc gcgttcgccc agcgaaaggg tgacgccaac gcctactcgc tgtcggtcgg     180
```

-continued

```
agaggtcgcc aaccgggcat gggaggccca cttcccgggg ccaccgaant atgcatgcag    240
ggcgggtatc aatccnagct acggtcaccg gctacnccga tctggtncgt gccgtcaagg    300
cgcgggtgcc ctccatgcat gtgcacgcnt ttnccccnat gganatcgcc aacggcntca    360
ccaa                                                                 364
```
<210> SEQ ID NO 51
<211> LENGTH: 321
<212> TYPE: DNA
<213> ORGANISM: Mycobacterium tuberculosis
<220> FEATURE:
<221> NAME/KEY: modified_base
<222> LOCATION: (1)...(321)
<223> OTHER INFORMATION: n = any nucleotide

<400> SEQUENCE: 51

```
gttctcactt gattgtccga atgtacaacg cgttattgga agcggtgttc tggttcttgt     60
cccgcaanac accggtgttc gtgaaatggc tgctgcgccg taccgcnatc aaaaatctgc    120
ccgagggcta caacatcnaa acccacttca cnccgcggta caacccgtgg gatcagcnac    180
tgtgcctgat cccggacgcc nacctgtaca acgccatcac cagcggccgc gccnaggtgg    240
tcaccgacca tatcaaccac ttcaacccac cggttattgc actcaaatcc ggtggggcac    300
ctcgatgcgg acattatcgt c                                              321
```
<210> SEQ ID NO 52
<211> LENGTH: 540
<212> TYPE: DNA
<213> ORGANISM: Mycobacterium tuberculosis
<220> FEATURE:
<221> NAME/KEY: modified_base
<222> LOCATION: (1)...(540)
<223> OTHER INFORMATION: n = any nucleotide

<400> SEQUENCE: 52

```
agcctcggcg gcctcgctgc tcagcaacgg cgttttcaat ttcactgcga gcgcagcgca     60
ttgaccgtag tgcggcgtcg agggtggcca gcgcccgcgg gcggcgcaac tgtcgtgcga    120
cctccacggc agtccatgcg ggcgcggtcg cgagacgacc tgacacccgt tggagccggg    180
caccgacgcg ttggtggacc atcagaccga ccgtgggccg catccttact ccgggatcga    240
ncatatggat agcgacggtg ttttccgtgt cnaatccata caacgcggcg ggggtgccca    300
gacacgcgac ggcgtgcccc cccatgaaca catcgagagc cgccaagcgg cccaacaggt    360
ccggctcttg tgccgcgtan acccgtacca aacgcgaacg aagccgccgt ttttcacttg    420
gacatccagc tgttggcggg tcatgaccgt gagcaattgc gcggtggtgg cgaaccgccg    480
gccttctcga gaattgttag cgcgtcggta ggcaccgtcc gancatgcga ngancgcctc    540
```

<210> SEQ ID NO 53
<211> LENGTH: 540
<212> TYPE: DNA
<213> ORGANISM: Mycobacterium tuberculosis
<220> FEATURE:
<221> NAME/KEY: modified_base
<222> LOCATION: (1)...(540)
<223> OTHER INFORMATION: n = any nucleotide

<400> SEQUENCE: 53

```
agagtaggca cggagcgtgc accgacaaca ccggcacgcg gtagcggcgc nacagcttcc     60
ggacggcatc aatntcctga ctgaccgatt caccccaaac catcagctcg acccgtcnta    120
```

```
ccaagcctgt cggcnttact cnaacncggc ctcggcccgc aaacgggtac accgaggccg    180
tcnacaagcc nactttgatt gctgggcgca ctgtgtgtgg tggcggctan cccnattgca    240
acaaggccag cggtcccagg gttatcagcg ccccaccgc aaccgcgata acgtactgg     300 cnatttcttc ggtcttgcgg actgcccgcn ccgagaccac taggccaagg atgaccatca    360
ccgatagcac tagcgccact atctgttcca gcgcccaac tgntcnaagg cgataaacaa     420
cccggcacga aggcaacgg ccaggatcaa ntgcagcacn accaaangcc cgcgcccag     480 cgtcgggaac nctccaggc acnaacgggg naccgcgcc tcggccggca catcaccctc     540
```

<210> SEQ ID NO 54
<211> LENGTH: 501
<212> TYPE: DNA
<213> ORGANISM: Mycobacterium tuberculosis
<220> FEATURE:
<221> NAME/KEY: modified_base
<222> LOCATION: (1)...(501)
<223> OTHER INFORMATION: n = any nucleotide

<400> SEQUENCE: 54

```
acggagcgtg caccgacaac accggcacgc ggtagcggcg cnacagcttc cggacggcat     60
caatntcctg actgaccgat tcaccccaaa ccatcagctc gacccgtcnt accaagcctg    120
tcggcnttac tcnaacncgg cctcggcccg caaacgggta caccgaggcc gtcnacaagc    180
cnactttgat tgctgggcgc actgtgtgtg gtggcggcta ncccnattgc aacaaggcca    240
gcggtcccag ggttatcagc gccccaccg caaccgcgat aaacgtactg gcnatttctt    300
cggtcttgcg gactgcccgc nccgagacca ctaggccaag gatgaccatc accgatagca    360
ctagcgccac tatctgttcc agcgcccaa ctgntcnaag gcgataaaca acccggcacg    420
aaaggcaacg gccaggatca antgcagcac naccaaangc ccgcgcccna gcgtcgggaa    480
cnctccaggg cacnaacggg g                                             501
```

<210> SEQ ID NO 55
<211> LENGTH: 390
<212> TYPE: DNA
<213> ORGANISM: Mycobacterium tuberculosis
<220> FEATURE:
<221> NAME/KEY: modified_base
<222> LOCATION: (1)...(390)
<223> OTHER INFORMATION: n = any nucleotide

<400> SEQUENCE: 55

```
atacangact gggtacgacg acgacgacan gccatggcga tatcggatcc gaattcgcca     60
ccgccgctgg ggcggtagtg ccgcgccggg atctcaccgg ctggtccggg tattgacagg    120
tcggtcacgt cgacgtggat ctgcggaccg ggcatgcgca gcctcgtgcc gaattcgagc    180
tccgtcgaca gcttgcggc cgcactcgag cccgggtgaa tgattgagtt taaaccgctg    240
agcaataact agcataaccc cttggggcct ctaaacgggt cttgagggt tttttgctga    300 aaggaagact atatccggat acctggcgta atagcgaana gcccgcaccg atcgcccttc    360
ccaacagttg cgcagcctga atggcgaatg                                    390
```

<210> SEQ ID NO 56
<211> LENGTH: 505
<212> TYPE: DNA
<213> ORGANISM: Mycobacterium tuberculosis
<220> FEATURE:
<221> NAME/KEY: modified_base
<222> LOCATION: (1)...(505)
<223> OTHER INFORMATION: n = any nucleotide

<400> SEQUENCE: 56

```
agggatacnc tgcaccagcg cgcggaattc gccgccgagc ttgccgagct gggccccnac      60
aaaggtcccg ctnaacttcc tcaacccgcg gcccggtacc ccgttcgccg acctggaggt     120
aatgccggtc ggtnacgcnc tcaaggcggt ggccgccttc cggttggcnt taccgcgcac     180
catgctgcgt tcgccggtg gccgcgagat caccctgggt gacctcggcg ccaanngagg      240
catcctgggg cggnatcaac gccgtgatcg tcggcaanta cctngaccac cctcggccgg     300
cccgcgnaaa ccgacctgga atgctcnaca aagctacaga tnccgctgaa ggcactcaac     360
nccagcctgt aantggtgga atcgtggct ggaaaacaac cgctccggtc gctgccggcg      420
tgtacanacg tgtacaccng ggnaactggc ggataccggc acccaacagc ggtncgaatg     480
ggtctggaac ccccggttc tgtgc                                            505
```

<210> SEQ ID NO 57
<211> LENGTH: 658
<212> TYPE: DNA
<213> ORGANISM: Mycobacterium tuberculosis
<220> FEATURE:
<221> NAME/KEY: modified_base
<222> LOCATION: (1)...(658)
<223> OTHER INFORMATION: n = any nucleotide

<400> SEQUENCE: 57

```
cgagccccag cagcataaat ggcgcgatga agaattctgg gattcgctgc ccagatactc      60
gtgcacccgc tcacccgcgc gtgtgatggc cacgacggca tggattggcg gggcgatcca     120
cgcccacagg ccaccgacca acacaccggt cgccgacaga cccagcatca caaacaggac     180
cgcccgtgtc cgcgacgtcc gcggtgcacc ggangctcgg acggtccgcc aaaaccgggt     240
ggctcggtca ccgctgtgtc ccaagtcggc cgantccacc tgcccgtggc gagaacagcg     300
cgcccaccag ccgtcgggcc ggacctggac gaccatccgg cgaccgcact gcgcacagaa     360
ccgggggggc tccagaccca tccgagccgc tgtcggcgtg gccgtatccg ccagttcccg     420
gtgtacacgt tgtacacgcc ggcagcgaac ggagcgcgtt gttttccagc cacgatttcc     480
accatttaca ggctggcgtt gaattgcctt cagcggcatc tgtngctcgt caacanttcc     540
aggtcggctt ccgcgggncg gncgaaggtg gtcaggtatt nccnacaatc acggnttnat     600
gccgccaagg atgcctccct tgggcgccca agtccccagg gtnatctcnc ggccccccg     658
```

<210> SEQ ID NO 58
<211> LENGTH: 370
<212> TYPE: DNA
<213> ORGANISM: Mycobacterium tuberculosis
<220> FEATURE:
<221> NAME/KEY: modified_base
<222> LOCATION: (370)...(0)
<223> OTHER INFORMATION: n = any nucleotide

<400> SEQUENCE: 58

```
gacggatttc acagtgttat ccgcagaata tccgataaaa acacgcgcgt tggtccgtcg      60
cccacnttgt tcggcnnagc agatcaggat gaccgtgtcg ggcggatgcg gccgactccg     120
ggcaaccagc agccaacgga gattcgccna gagcctcctt tgctgcctgg gtccgcacag     180
cgctcgtcag gcgacctgag ggcggtcggc gccccgcaa agacacttcc ggaagcggta     240
caagatgctc ccgggatggc ccggcgcgac cgacnaccgc tcggggcgtg tcnantcatc     300
tnctggtgtc cacaacggtt ggccgccgcc gacnaatttg cgccacccgc accgatatccg    360
```

```
ccntagttgc                                                                370
```

<210> SEQ ID NO 59
<211> LENGTH: 343
<212> TYPE: DNA
<213> ORGANISM: Mycobacterium tuberculosis
<220> FEATURE:
<221> NAME/KEY: modified_base
<222> LOCATION: (1)...(343)
<223> OTHER INFORMATION: n = any nucleotide

<400> SEQUENCE: 59

```
agtaatanaa ttcgctcgat tggtgccgct gtcagtgttc tcgccgtcta cccgcatcca        60
ntcggcggtg cggccagcaa ggtaaatcca gccttcanan tccggtatg cnaggtctcc        120
agaccantac atgccgtggc gcatgcgctc ggcgttggct tcgggtcat tgtantagcc        180
ggtgaanaaa cccgaccccg tcgtgttgac canctcacct atggcttcat cggcgttggt      240
gagtgctccg tgagcgtcaa accgcncnac gncccactcg gtgacggttt cgccgttgta      300
caccgcgacc cgtgggctcc ccggccnatc nagcccggtg gcg                          343
```

<210> SEQ ID NO 60
<211> LENGTH: 706
<212> TYPE: DNA
<213> ORGANISM: Mycobacterium tuberculosis
<220> FEATURE:
<221> NAME/KEY: modified_base
<222> LOCATION: (1)...(706)
<223> OTHER INFORMATION: n = any nucleotide

<400> SEQUENCE: 60

```
aattcngcac gagcaccttc tcggccacca cgcccggctc cagcccggag ttgaangcga        60
tctgcttcag cggggcctcc ancgccacct tcacgatgtt ggcgccggtc gcctcgtcgc      120
cttcgagctt cagctcgtcc agggtcgggg ccgcttgcaa cagcgtcaca ccccaccgg       180
cgacatgccc tcctcgacgg cggccttggc attgcgaaac cgcatcctcg atgcggtgct      240
tgcgctcctt gagttcgacc tcggtggggg caccggcctt gatcaccgcg acaccaccgg      300
ccagcttggc cagccgctcc tgcagcttct cacggtcgta gtcggagtcg ctgttctcga      360
tctcctggcg gatctgggcc actcgtccgg cgatggcgtc ggtgtcaccg cgccctcga      420
cnatggtggt ctcgtccttg gtgaccacga acttgcgggc cttgcctaac agcgacaggt      480
cggcgttctc cancgtcagg cgacctctt cgctgatcac ctgaacaccg gtganaatgg       540
ncatatcctg caacatcgcc ttgcggcggt cgccgaaanc cgggaaccttg accgccacc      600
gacttgaaag gtgccgcgga tcttgttgaa caacangggt gganagcgcc tcccctcaac      660
ttctcngcna taatcagcag cgggttaccg gttccaataa cttccc                    706
```

<210> SEQ ID NO 61
<211> LENGTH: 261
<212> TYPE: DNA
<213> ORGANISM: Mycobacterium tuberculosis
<220> FEATURE:
<221> NAME/KEY: modified_base
<222> LOCATION: (1)...(261)
<223> OTHER INFORMATION: n = any nucleotide

<400> SEQUENCE: 61

```
agggccaccg ccgcggtgtg ggacgcggcg cgagccttag acgacgcggg cgaatctacc        60
tccgacgtcg aattcgcggc ggcggtggcg gcnacgctgg caccggcgac cgctcagcgc      120
tgcacgcagg actgcattca ngtgcacggc ggcatcggct tcacctggga gcatgacacg      180
```

```
aacgtctact accgccgggc gttgatgctg gccgcgtgct ttggccgcgg ctcggagtat    240
ccgcagcggg tggtggacac c                                             261
```

<210> SEQ ID NO 62
<211> LENGTH: 125
<212> TYPE: DNA
<213> ORGANISM: Mycobacterium tuberculosis

<400> SEQUENCE: 62

```
gtcttgacca cggttccgag gaaccgttcg cccaccgtcg gcagctgcgg gttggcgatg     60
gcgttgatct tgtcgatcgc ggcctgtgcc gatggccgtc ggtggcgccg acaaacacgg    120
tgccg                                                               125
```

<210> SEQ ID NO 63
<211> LENGTH: 402
<212> TYPE: DNA
<213> ORGANISM: Mycobacterium tuberculosis
<220> FEATURE:
<221> NAME/KEY: modified_base
<222> LOCATION: (1)...(402)
<223> OTHER INFORMATION: n = any nucleotide

<400> SEQUENCE: 63

```
agcgcacggc catgaanatg cgcggcatca gcgggaagtg aaggccatgt ggcactcgtc     60
gccaccggtg ttgggatcac cgaaatattc gacgacatcg cccgggccac tgattggctt   120
cggctagcag cacccggccg gggaattcgt cgtccaccac cttgcggact ccttgaaaaa   180
agcgtgtgtt tccggcagtt ctcgcagttg gtgcctcacg ttcaaanana tagggccgc    240 ntccaccgaa acccgtcaag cccaagccga gccnaaagcg gatgactcaa tcatcgcctc   300
ttgcacgcgg ggttgtcgta tccaaatccg gttggtggga gaagaatcgg tgccagtaaa   360
ctgtcggngg acnggatcaa tgacagttca ctcttcggtg tc                      402
```

<210> SEQ ID NO 64
<211> LENGTH: 381
<212> TYPE: DNA
<213> ORGANISM: Mycobacterium tuberculosis
<220> FEATURE:
<221> NAME/KEY: modified_base
<222> LOCATION: (1)...(381)
<223> OTHER INFORMATION: n = any nucleotide

<400> SEQUENCE: 64

```
agcaagtctc ggcatctcca ccggcgacgt gatcaccgcg gtcgacgcg ctccgatcaa     60 ctcggccacc gcgatggcgg acgcgcttaa cgggcatcat cccgtgact catctcggtg   120 anctggcaaa ccaagtcggg cggcacgcgt acagggaact gacttggccg agggaccccg   180
gctgattcgt ccggatacca ccgcnggcgg gcaattggat tggcgccagc cgtgatggcg   240
ctnagccccg aattcctctc cgtgcgcgtg gctctggaac catgaacaag caaacacagc   300
gtcgagcacc tcccgtgcag ggcntcacgt cnaaggcgtg tggtcaacat ccggatgcaa   360
ggattcggca gcgccgccgc c                                             381
```

<210> SEQ ID NO 65
<211> LENGTH: 434
<212> TYPE: DNA
<213> ORGANISM: Mycobacterium tuberculosis
<220> FEATURE:
<221> NAME/KEY: modified_base
<222> LOCATION: (1)...(434)

<223> OTHER INFORMATION: n = any nucleotide

<400> SEQUENCE: 65

| | | | | | |
|---|---|---|---|---|---|
| taatgccgat | gcctggtcna | tcgacgcacc | ttcaccccgg | accagcaggc | ccatcgcnag | 60 |
| gcggaggcgg | acttgttcta | cagcgacttc | gtggaacgcg | tcgccgaggg | ccgcaagatg | 120 |
| actaccgacg | ccgtggacnt | cnttgcgcna | ggccgggtct | ggaccggtgc | cgacnctctc | 180 |
| natcgcggcc | tggtcnacaa | actcgcggcc | ttcaaccgcg | gtgcgtcncn | cgaaggtcta | 240 |
| ccggactaaa | taaggacccg | aggttccata | ntcagttatc | cggggtcgtc | actctgggac | 300 |
| atggtgcgac | cgcgtccgtc | gtcacaacgg | cagcgcatcg | ctgccggatg | ctatgggtgc | 360 |
| ctgcttgccc | gttcgatcgt | cgcatcgtca | agcaggtgaa | caaanctcag | tggtgccagc | 420 |
| gtgttgtggg | tggg | | | | | 434 |

<210> SEQ ID NO 66
<211> LENGTH: 424
<212> TYPE: DNA
<213> ORGANISM: Mycobacterium tuberculosis
<220> FEATURE:
<221> NAME/KEY: modified_base
<222> LOCATION: (1)...(424)
<223> OTHER INFORMATION: n = any nucleotide

<400> SEQUENCE: 66

| | | | | | |
|---|---|---|---|---|---|
| caccaccttg | gccggcatcg | gcgccaagcc | caccgccatt | cggcgcacgg | tgtacatcga | 60 |
| cttgcgcgcg | gactggccgg | cggcactgca | agctgccggc | ctggactcga | cgcaccgaca | 120 |
| gcatggttgg | ccgaagcatg | ctgatctacc | tgccgccgga | tccaggaacg | gttgttcgac | 180 |
| aacagcaccg | aactcagtgt | tgcgggcagc | acgatcgcta | ccgaattgtc | ccgggcattg | 240 |
| tggattcgac | cangccgggt | acaaaaatgg | cggattcttt | cgcaagcacg | cgtggactca | 300 |
| catggcgtcc | tggtgtattc | cggcaacgca | ccacgtctcg | actactgcgc | gccaagggct | 360 |
| gggacttgaa | ggcacagtgc | ggaccaacta | ttcagcgcaa | tggtttgccg | ttcccgcccc | 420 |
| acac | | | | | | 424 |

<210> SEQ ID NO 67
<211> LENGTH: 596
<212> TYPE: DNA
<213> ORGANISM: Mycobacterium tuberculosis
<220> FEATURE:
<221> NAME/KEY: modified_base
<222> LOCATION: (1)...(596)
<223> OTHER INFORMATION: n = any nucleotide

<400> SEQUENCE: 67

| | | | | | |
|---|---|---|---|---|---|
| caccggggct | cnantgcggc | cgcaatcttg | tctacagatc | tcgaattcng | cacgagcggc | 60 |
| acgagaagcn | ganaccgatg | tgcgcgaagc | gcaacctggg | cgcggcngag | cgccacgccg | 120 |
| cagcggcggc | ggccggcacc | gactttcaan | ggtgatggtg | cggccnaggc | gcgggttgcc | 180 |
| cgtcntgccc | tgganttggt | cccgacctgt | ggcgcggcgc | gttggtcgtg | ctgcagtcaa | 240 |
| tcctggccgt | tgccttcggt | gccgggttgt | tcancgcctt | caacaattgt | ggcgctggaa | 300 |
| cagcatantg | gcnctatgct | atcggtgatg | gtcancttgg | cctagtggtc | tcggtgcggg | 360 |
| cagtccgcaa | naccaaaaac | atcccagtta | ctttnatccc | gttgcggtgg | gggcctnatt | 420 |
| acctgggacn | ctggcttgtt | gcaatcgggc | tagccgccac | cacacacagt | gccccagcan | 480 |
| tcaaantcgc | ttgtcacgct | cgtgtaccgt | tgcggccagg | cccntcgaat | acncnacggc | 540 |
| ttggctacaa | cgggtcaact | ganggtctgg | ggtgaacgtc | attcggacat | caatgc | 596 |

<210> SEQ ID NO 68
<211> LENGTH: 233
<212> TYPE: DNA
<213> ORGANISM: Mycobacterium tuberculosis
<220> FEATURE:
<221> NAME/KEY: modified_base
<222> LOCATION: (1)...(233)
<223> OTHER INFORMATION: n = any nucleotide

<400> SEQUENCE: 68

```
atcgtcaaac tgacaccaac ccccatcacc ggccacaccg ancaaatccg gccccagctg      60
cccggcanna tcggcaccgg cgcaccatca ccaaactcat cggccaacac cgtcaacccg     120
ccggctgccc aaccgactcc ttgccagccg tcccaacaaa cccaacgccc cagcacccga    180
tcagaaccca acancgacac cgaagtgctc gcgggaccg ggtccaccgc cga            233
```

<210> SEQ ID NO 69
<211> LENGTH: 401
<212> TYPE: DNA
<213> ORGANISM: Mycobacterium tuberculosis
<220> FEATURE:
<221> NAME/KEY: modified_base
<222> LOCATION: (1)...(401)
<223> OTHER INFORMATION: n = any nucleotide

<400> SEQUENCE: 69

```
ggacaccgtt cacaagggcg tttcgagcaa cgcgtcgacg caacttcggc ctagtcgacg      60
ttgacnggtt cgttccattt cgactgcgtg agctgaatcg accggatccg aggtcgatgc     120
tcgctcggac gaggtggtgc gagccgtcct gggcaatcca cacggtcgcc ggccttgcac    180
tcttggcgcc aggatcaanc atcttgacag agctcgcggg gatggtcccg gtgatttggg    240
tggtcnaaat tcntctatca cttcggtacc ttgcgcttgg aggttcgtga caccggacag   300
cagctgcgtc acccancggc aggatcnagc acgcntgaag ttgacannca gaaatcnagc  360
cgagattgct cagtcgtcga acagttcacc gagatgttgt c                       401
```

<210> SEQ ID NO 70
<211> LENGTH: 306
<212> TYPE: DNA
<213> ORGANISM: Mycobacterium tuberculosis
<220> FEATURE:
<221> NAME/KEY: modified_base
<222> LOCATION: (1)...(306)
<223> OTHER INFORMATION: n = any nucleotide

<400> SEQUENCE: 70

```
gccgagatct ggcccgcatg agccgcagcg ggctggctcc gatgagccct gccgaagcgg      60
tggaattgtt tgacgctgcg ctggccatcg atcaccctct ggcggtggcc acgctcttgg    120
accgggctgc actagacgcc cgggcccagg gcggtgcgtt gccggcgctg ttcagcgggc   180
tcgcgcgccg cccacgccga cgccaaatcg acnacccggt gacccacctc gtcgaagtcg  240
gngctngttc accctacacg ggctggncgc ggacaacaac tcnactgctn ntggggctng 300
tgtgtc                                                             306
```

<210> SEQ ID NO 71
<211> LENGTH: 241
<212> TYPE: DNA
<213> ORGANISM: Mycobacterium tuberculosis
<220> FEATURE:
<221> NAME/KEY: modified_base
<222> LOCATION: (1)...(241)

-continued

<223> OTHER INFORMATION: n = any nucleotide

<400> SEQUENCE: 71

| cgcgctacng | tgaccgtctt | cgtcggaccg | ttgcggtgtt | tgggcgagaa | tgaaatccgc | 60 |
| ttctccccca | cgtggatcgt | cgcggtcaaa | ggcgtcgggt | cgatgcagca | ggatnacaac | 120 |
| gtcggcatct | tgttccagcg | aattgtgcaa | actaatgcca | ttggcgacga | aattgtgtgt | 180 |
| gccgcttaca | gtcccatcga | aaacatgttg | atctccaatg | ctggtgatct | ccacgacggt | 240 |
| g | | | | | | 241 |

<210> SEQ ID NO 72
<211> LENGTH: 384
<212> TYPE: DNA
<213> ORGANISM: Mycobacterium tuberculosis
<220> FEATURE:
<221> NAME/KEY: modified_base
<222> LOCATION: (1)...(384)
<223> OTHER INFORMATION: n = any nucleotide

<400> SEQUENCE: 72

| aggctcgggt | tagccgcgtg | tgctcctcgt | gatccagcag | gncttcggat | agcgattcgg | 60 |
| cgatcatctc | ggacagttcc | gcagtggaga | cggcgatgtc | aanttcatcc | ttcggctgca | 120 |
| ccccaaccag | ccgcagtatc | gcgttggcgc | agttgttgta | naaccgatga | acggccgggc | 180 |
| gaggcgcacg | tanaccaggt | aggcgggacc | agcaacatcg | ctgttcgctc | cggaacagcc | 240 |
| aaancgatnt | cttcggcaca | tctcaccgag | caggacatgc | agcgccacca | cgatcgccaa | 300 |
| cnacaaggtg | tgcagcagcg | ccggcggtac | accgctcagc | ccgaacgacg | ctgtancagc | 360 |
| ttgacnactg | ccggttcgcc | gacc | | | | 384 |

<210> SEQ ID NO 73
<211> LENGTH: 411
<212> TYPE: DNA
<213> ORGANISM: Mycobacterium tuberculosis
<220> FEATURE:
<221> NAME/KEY: modified_base
<222> LOCATION: (1)...(411)
<223> OTHER INFORMATION: n = any nucleotide

<400> SEQUENCE: 73

| tgcaccttga | ccagcagccg | ctggtcggtg | ctggcgacng | ttccgggtgc | ctcggggaac | 60 |
| angccnatta | cccggtctcc | gaccgcgaaa | gatccttgtt | caagctggtt | tcgataacga | 120 |
| cgccgcangc | ctcaacgccc | atgancgcgt | ccggatcggg | atacagacca | gcgcgatcat | 180 |
| gacgtcgcgg | aantggcggc | aatcgcggac | accgcaactc | gaactgcccg | gggccagcgg | 240 |
| cgcgtcgcat | cgggaatcag | ctccaccgca | gattctcgaa | ggtgccggcg | gtgctcatcg | 300 |
| ccaaccgcca | cgccggtcac | tcggangaac | aacagcccgc | ccaccgcgcg | gctaccgtgc | 360 |
| accgcgccgt | ataaacctcc | cgcgccgcca | caacacctgc | ggtcgcctgt | c | 411 |

<210> SEQ ID NO 74
<211> LENGTH: 196
<212> TYPE: DNA
<213> ORGANISM: Mycobacterium tuberculosis
<220> FEATURE:
<221> NAME/KEY: modified_base
<222> LOCATION: (1)...(196)
<223> OTHER INFORMATION: n = any nucleotide

<400> SEQUENCE: 74

| agaggacttc | gggccggcga | acgcgcggaa | gatcctanac | acatacggca | cggattactg | 60 | cgtgttcnac gatgacatgc aaggaaccgg cgcggtggtc ttggccgccg tatacagcgg        120 tctgaangtt accggtatcc cgctgcgcga tcagacaata gtcgtcttcg gcgcangcnc        180 cgcagggatg gggatc                                                       196

<210> SEQ ID NO 75
<211> LENGTH: 559
<212> TYPE: DNA
<213> ORGANISM: Mycobacterium tuberculosis
<220> FEATURE:
<221> NAME/KEY: modified_base
<222> LOCATION: (1)...(559)
<223> OTHER INFORMATION: n = any nucleotide

<400> SEQUENCE: 75
acggcggcct ggttgatgaa cattaagcct tgcgcgacca accgcgtgc gcacagcacc          60 gcgaccgacn acgcgatgaa caccaccaca cccatgcgca tcggtccgga accaagcaga       120
gcatgcacgc cagcacccag cacgatcccc agcgccaccc cgacgatcat ctgttgggca       180
cgtcgtgcgc gcaacacgtt ggtcgccgac atgcacacca cagccgaaat cggcgcgaan      240
aacgctgcgg atggttgaac cgtcatgggt naanatacca cgcgaaggcg gcgacgaccg      300
atgtctgggt gatcggncac agcacggtgc gcaaccgttg ggcgaacgca cngncgcccg      360
cagggccgtc ctgactagca acgaancgct catgaacgnc ctatttattc acactcnggt      420
gcgaacgtct taaccgcaaa gatcctggtc atgcctgctg gaacccttgg ggcttgggca     480
tctnttccgg aactccttac ttgctnaacg ttaatgggcg ccngngcttc ggtaacggat      540
caaccccgcc gccggtctt                                                   559

<210> SEQ ID NO 76
<211> LENGTH: 464
<212> TYPE: DNA
<213> ORGANISM: Mycobacterium tuberculosis
<220> FEATURE:
<221> NAME/KEY: modified_base
<222> LOCATION: (1)...(464)
<223> OTHER INFORMATION: n = any nucleotide

<400> SEQUENCE: 76
gtgcctggcg gggcgtcgca gccgcggcgc acgctggacg gctggcagga ctgggccaag        60
cancncggcc accgcgnact ggcctacttt gctggtcgcc naaaaacggc acgctgggcg      120
gtccggtggc caaaaacctg accnaggcca ancgcaccgg actggccgac catttcgggg      180
ccaaaccggc aattgcatct tctnctcggc cggtccggtc aaatcgtcgc gggcactgct      240
gggccggccc cntcaaaatc gcaaccggct gggcctgatt gacccnatgc ttgggcattc     300
gnctgggtcg ttaccnccg ctgttcnagc cggccnacaa aacnaccgcc gccggtaagg      360
tccggtcggc tcggggcct ggaccgcggt gcaccatgcc ttcaccgccc cgaaccgga       420 atgggangac cgcatcnant ccgatnccgg cacntgctgg ccga                       464

<210> SEQ ID NO 77
<211> LENGTH: 618
<212> TYPE: DNA
<213> ORGANISM: Mycobacterium tuberculosis
<220> FEATURE:
<221> NAME/KEY: modified_base
<222> LOCATION: (1)...(618)
<223> OTHER INFORMATION: n = any nucleotide

<400> SEQUENCE: 77

-continued

```
gacgttgtga ggggtcaacg aagaccccg gatgagagtc caaccgattc ggtgatgtgt      60
ccacacgacg aacggatttc acaggttatc cgcagaatat ccgatgaaaa cacgcgcgtt    120
ggtccgtcgc ccacgtgttc ggcgagcaga tcaggatgac cgtgtcgggc ggatgcggcc    180
gactccgggc aaccagcagc caacggagat cgccgagag cctcctttgc tgcctgggtc     240
cgcacagcgc tcgtcaggcg accctgaggg cggtcggcgc ccccgcaaag acacttccgg    300
aagcggtagc aagatgctcc cgggatggcc cggcgcgacc gacgaccgct cggggcgtgt    360
cgagtcatct tctggtgtcg cagcagcggt tggccgccgc cgacgagttt gcgccacccg    420
caccgatacc gccgtagttg ccgcggncag caccacccgc cgctgtcacg gcgatggcaa    480
ccgatctgaa gcccaacgcg tcgtcnaaca gcaaaccaca gttccgaaca gcaaggaaca    540
gcaggncagt cnggaactgc agcaaccgct nccnggaagg ggcccgttgc ancaacagcc    600
cttgcgccga tcgccagg                                                  618
```

<210> SEQ ID NO 78
<211> LENGTH: 616
<212> TYPE: DNA
<213> ORGANISM: Mycobacterium tuberculosis
<220> FEATURE:
<221> NAME/KEY: modified_base
<222> LOCATION: (1)...(616)
<223> OTHER INFORMATION: n = any nucleotide

<400> SEQUENCE: 78

```
gtgaccttgg ccagcgatca ccactgggcc ggcgtatgga tcggcaccac cctgggcatg     60
atcctggccg acggcctggc gatcggcgca gggctgctgc tgcaccggcg ccttccggag    120
cggttgctgc aggtcctgac tggcctgctg ttcctgctgt tcggactgtg gttgctgttc    180
gacnacgcgt tgggcttcag atcggttgcc atcgccgtga cagcggcggt ggtgctggcc    240
gcggcaacta cngcggtatc ggtgcgggtg gcgcaaactc gtcggcggcg gccaaccgct    300
gctgcgacac cagaagatga ctcgacacgc cccgagcggt cgttcggtcg cgccgggcca    360
tcccgggagc atcttgctac cgcttccgga agtgtctttg cggggcgcc gaccgccctc     420 agggtcgcct gacnagcgct gtgcggaccc aggcagcaaa ggaagctctc ggcgaatctc    480
cgttggctgc tggttgcccg gantcggncg catccgcccg acacggtcat cctgatctgc    540
tcnccaaaca cnttgggcaa cggaccaacg cccnttttt catcggatat tctgcggaat     600
aacctgttaa atccgt                                                    616
```

<210> SEQ ID NO 79
<211> LENGTH: 460
<212> TYPE: DNA
<213> ORGANISM: Mycobacterium tuberculosis

<400> SEQUENCE: 79

```
agggaattgc gccgcggacc accgcgtgcg aagccgagca cgcagccccg tccgatggtg     60
gtgccgcgca gcacgctcac cttcacgccg atccaggtgt cgggcccgat ccgcaccgga    120
ctcttgatga tgcccctggtc tttgatcggc agcgtgatgt cgtccatccg gtggtcgaaa    180
tcgcagatat agcaccagtc ggccattagc accgagtccc cgatctcgat gtcgagatag    240
gtgttgatga agttgtcccg gcccagcacc accttgtcgc cgaaccgcag cgagccctcg    300
tgggcacgga tcgtgttctt gtccccgatg tgcacccagc ggcgatctc cagttgcgct    360 agttccggtg tcgcgtggat ctccacaccc ttgccgaaaa acaccatgcc gcgggtgatg    420
atatgcgggt tggccacttg aacctcaaca gccgccagta                          460
```

<210> SEQ ID NO 80
<211> LENGTH: 593
<212> TYPE: DNA
<213> ORGANISM: Mycobacterium tuberculosis
<220> FEATURE:
<221> NAME/KEY: modified_base
<222> LOCATION: (1)...(593)
<223> OTHER INFORMATION: n = any nucleotide

<400> SEQUENCE: 80

```
gactttgacg atggtgcctt cgacgatgtc gccatcgttg aagtacttga tcgttttgtc      60
tattgcggcg agaaagtcct cgctagagcc tatgtcgttg acggctactt gcggcgaggt     120
gacggtggga ctcggcatat tgttgggttg ctccggacag ggttgggtcg tanggacaga     180
ttggtacctg acgaggctac tcgacgggta cacgctggac aaactcggtc ccgattgcgc     240
cgagcgtgaa ctcagggcgg aaaaatcgcc gaattcccgc cccagatgca cgctcggcac     300
tcagtgcgcc gccgcgtccc agctgcggcc gtagcccacc gacacctcca gcgggacgtc     360
gagcgggtaa gcgccgccca tcttgtcgcg caccanggcc tcgacccgct cgcgttcacg     420
ggggcgattt cgaacagcag ctcgtcgtgg anctgcagca gcatgcgcga cgccngctgt     480
gcctcgttga ncgccttgtc nacctggatc atggncacct tgatnatntt cggcgcgctt     540
gccctggatc ggngcgttca ncggccgccc gctcgggggg ctcccgcact tga            593
```

<210> SEQ ID NO 81
<211> LENGTH: 602
<212> TYPE: DNA
<213> ORGANISM: Mycobacterium tuberculosis
<220> FEATURE:
<221> NAME/KEY: modified_base
<222> LOCATION: (1)...(602)
<223> OTHER INFORMATION: n = any nucleotide

<400> SEQUENCE: 81

```
gctgctcgcc caccgcgacg tcacccggct caaggtcacc gtcgacgggt tgctccaagc      60
ggtggccgcc gacggccgca tccacaccac gttcaaccag acgatcgccg cgaccggccg     120
gctctcctcg accgaaccca acctgcagaa catcccgatc cgcaccgacg cgggccggcg     180
gatccgggac gcgttcgtgg tcggggacgg ctacgccgag ttgatgacgg ccgactacag     240
ccagatcgag atgcggatca tggcgcacct gtccggggac gagggcctca tcgaggcgtt     300
caacaccggg gaggacctgc attcgttcgt cgcgtcccgg gcgttcggcg tgcccatcga     360
cgaagtcacc ggcgagctgc ggcgccgggt caaggcgatg tcctacgggc tggcttacgg     420
gttgagcgcc tacggcctgt cgccacantt gaaaaatctc caccgaggaa gcccacgaac     480
anatgggacg cgtntttcgc ccgattccgg ggggtgcgca actaccntgc gccgcccta     540
ttcaaacggg gcccgcaagg acggntacnc ctccacggtg cttggggcct tccccgctac     600
ct                                                                     602
```

<210> SEQ ID NO 82
<211> LENGTH: 506
<212> TYPE: DNA
<213> ORGANISM: Mycobacterium tuberculosis
<220> FEATURE:
<221> NAME/KEY: modified_base
<222> LOCATION: (1)...(506)
<223> OTHER INFORMATION: n = any nucleotide

<400> SEQUENCE: 82

| | |
|---|---|
| ccatcatcag cgcgctggct cgggtgcggt gcatgagaag tgcacccgc tcggtgcgtt | 60 |
| cgtgctcgac ggcctgtagc ggcctgtcca ggatggccga cacccgcggg tcggccgagg | 120 |
| tctccggtac gtcctcgttg gtgacgagtt cggactgcac ggtcacgcga acgaattcct | 180 |
| cgattgcctc gacgacgtac tcgatcgccg cgacgctgcg gtgggccagc gacaccagcc | 240 |
| gggtggacgt cactttgact tgcttgcccg ccggtgagcg ccagtgcgcg cggcgggtca | 300 |
| gcgtcccggc gcgcaggtcg aggatccgtt cgtgggagat caattcgcca taccggacgt | 360 |
| cgaacggctc gtcgccgacc aacaggcgaa agatcttgcc gttggtgacg tcnacaacgg | 420 |
| tctggccggc ctccgggata ccataaccg gcctcggcgt tacggcagcg ggcgggattt | 480 |
| cgtanaaaga nttcaggtag gtgccc | 506 |

<210> SEQ ID NO 83
<211> LENGTH: 505
<212> TYPE: DNA
<213> ORGANISM: Mycobacterium tuberculosis
<220> FEATURE:
<221> NAME/KEY: modified_base
<222> LOCATION: (1)...(505)
<223> OTHER INFORMATION: n = any nucleotide

<400> SEQUENCE: 83

| | |
|---|---|
| ccgggcacct acctgaactc tttctacgaa atccggccgc tgccgtacgc cgaggccggt | 60 |
| tatggatatc cggaggccgg ccagaccgtt gtcgacgtca ccaacggcaa gatctttcgc | 120 |
| ctgttggtcg gcgacgagcc gttcgacgtc cggtatggca aattgatctc ccacgaacgg | 180 |
| atcctcgacc tgcgcgccgg gacgctgacc cgccgcgcgc actggcgctc accggcgggc | 240 |
| aagcaagtca aagtgacgtc caccggctg gtgtcgctgg cccaccgcag cgtcncggcg | 300 |
| atcgagtacg tcgtcgaggc aatcgaggaa ttcgttcgcg tgaccgtgca gtccgaactc | 360 |
| gtcaccaacg aggacgtacc ggagacctcg gccgacccgc gggtgtcggc catcctggac | 420 |
| aggccgctac aggccgtcga gcacgaacgc accgagcggg gtgcacttct catgcaccgc | 480 |
| acccgagcca gcgcgctgat gatgg | 505 |

<210> SEQ ID NO 84
<211> LENGTH: 634
<212> TYPE: DNA
<213> ORGANISM: Mycobacterium tuberculosis
<220> FEATURE:
<221> NAME/KEY: modified_base
<222> LOCATION: (1)...(634)
<223> OTHER INFORMATION: n = any nucleotide

<400> SEQUENCE: 84

| | |
|---|---|
| gaaatatccg atccgccaag tgccgccttc gcttccgcca ccgcggnatc aaccttgttc | 60 |
| ancgtgtctt cangtacctt cgaaccaccc tcggcctcac gctgttcttt gacgaacttc | 120 |
| tccgtctggt agaccaatgt ctcggcttga ttacgaacat cggcctcctc gcgacgcttg | 180 |
| cgatcctcct cggcgtgcgc ttcggcgtcc ttgatcatgc ggtcaatgtc ttccttggac | 240 |
| aggcccgagc cttcctggat tcggatcgtg ttctccttgc cggtgccctt gtccttggcg | 300 |
| gtgacgtgca caatgccgtt ggcgtcgatg tcgaaagtga cctcgatctg cggaatcccc | 360 |
| cgcggcgccg gcgggatgcc ggtcagctcg aaggacccga gcaacttgtt gtgcgcggcg | 420 |
| atctcacgct ccccctgata gacctggatc tgcaccgacg gttggttgtc gtccgcggtg | 480 |
| gtgaaagtct ccgaccgctt ggtggggatc ntggttgttg cnctcnatga acctggtcat | 540 |
| caccccgccc ttggtctcna tacccaaggc tcanccgggg gtaactcnag cagcaaaacg | 600 |

<210> SEQ ID NO 85
<211> LENGTH: 493
<212> TYPE: DNA
<213> ORGANISM: Mycobacterium tuberculosis
<220> FEATURE:
<221> NAME/KEY: modified_base
<222> LOCATION: (1)...(493)
<223> OTHER INFORMATION: n = any nucleotide

<400> SEQUENCE: 85

| | | | | | |
|---|---|---|---|---|---|
| accaacaang | gcgtcaaccc | cgatgaggtt | gtcgcggtgg | gagccgctct | gcaggccggc | 60 |
| gtcctcaagg | gcgaggtgaa | agacgttctg | ctgcttgatg | ttaccccgct | gagcctgggt | 120 |
| atcgagacca | agggcggggt | gatgaccagg | ctcatcgagc | gcaacaccac | gatccccacc | 180 |
| aagcggtcgg | agactttcac | caccgccgac | gacaaccaac | cgtcggtgca | gatccaggtc | 240 |
| tatcaggggg | agcgtgagat | cgccgcgcac | aacaagttgc | tcgggtcctt | cganctgacc | 300 |
| ggcatcccgc | cggcgccgcg | gggattccg | cagatcgang | tcactttcga | catcgacgcc | 360 |
| nacggcattg | tgcacgtcac | cgccnangga | caagggcacc | ggcnaggaaa | aacacgatcc | 420 |
| gaatccanga | aggctcgggc | ctgtccaagg | aaagacttga | ccgcatgatc | aaggacccca | 480 |
| aancgcacgc | cga | | | | | 493 | ttttcactt cncctttaag gaccccggct tgca 634

<210> SEQ ID NO 86
<211> LENGTH: 230
<212> TYPE: DNA
<213> ORGANISM: Mycobacterium tuberculosis

<400> SEQUENCE: 86

| | | | | | |
|---|---|---|---|---|---|
| gggggcgatc | tccaccggga | agccggccag | caccccaaca | acgtcaccaa | gaccgacacc | 60 |
| cgcggcggcc | aggccgcccg | cgatgcaacg | agcacgctca | tggacctcgc | cccaggtgtg | 120 |
| gcggacgggc | atgtgcggtt | cacctgtgac | catgcccgtc | gtcgcggtgc | gggcattgtg | 180 |
| gaacatcttc | tcggtgaact | gctcaaggca | acctcctcgg | ttccggtgct | | 230 |

<210> SEQ ID NO 87
<211> LENGTH: 561
<212> TYPE: DNA
<213> ORGANISM: Mycobacterium tuberculosis
<220> FEATURE:
<221> NAME/KEY: modified_base
<222> LOCATION: (1)...(561)
<223> OTHER INFORMATION: n = any nucleotide

<400> SEQUENCE: 87

| | | | | | |
|---|---|---|---|---|---|
| ggagacgatg | ccgggccgcc | ccgccgagct | cggcgccgca | ctcggcgccc | tcaccggcga | 60 |
| gctggccgcc | ctggaccgta | cggcattcgg | cacacgttgt | gcgggtttgg | gtttcgacga | 120 |
| ctatgccacc | gacaacctgt | ggcgactgct | ggacgaccaa | cgcaccgcta | ccgcagtggt | 180 |
| acccaccgac | agcacattgt | tggtcgagcg | gtttcgtgac | gagctgggcg | attggcgggt | 240 |
| gatcttgcat | tctccgtatg | ggctgcgggt | gcacggaccg | ctcgcgctcg | cagtcggccg | 300 |
| gcggctgcgc | gaccgctatg | gcatcgacna | naagccgacc | gcctccgaca | acggcatagt | 360 |
| ggtgcgccta | ccggacaccg | tgtccgctgg | cgaanacagc | ccgccgggtg | ccgaatgttc | 420 |
| gttttcgacg | ccgacnanat | cgaccgcgatc | gtcaccaccg | aaattggccg | gttcggcgct | 480 |
| gttcgcgtca | cggttccngg | aaatcggcgg | cccgccgctc | ttgctgctgn | cccgccggna | 540 |

```
cccccggccg ccgtcgccgc t                                               561
```

<210> SEQ ID NO 88
<211> LENGTH: 466
<212> TYPE: DNA
<213> ORGANISM: Mycobacterium tuberculosis
<220> FEATURE:
<221> NAME/KEY: modified_base
<222> LOCATION: (1)...(466)
<223> OTHER INFORMATION: n = any nucleotide

<400> SEQUENCE: 88

```
acactgctcg acgccggcgg tatcctttgg ccgcggtcac gaatncgccg cgcaccagcc      60
ggtnatcgct ggccagccgg cccagcacgt cggcggtcac ccgcagccca aaaccgaacc     120
gggctgcggn cgcagaggtg gtgaacggtg tgtgggtgcg tgcgtatcgg cccaataatt     180
cgcccagcgg gtcggctacc gcctcggtga anctggccgg caaccccanc ggaaccgccg     240
cgccaacncc gtcncgcanc cggcccatgt cctcaacggn aacccaccat tctgcggccg     300
gnntaangac accncgagcn cgcgtctggg gtgtgcntaa gccntcccaa ccagccgctg     360
accttcgggc gccccgccc gggncancga tctcgtcttc ngtgancgga cncancagcc     420
cgcagnacat cgggcaaccc cttngggcat cangggctac ccggtc                    466
```

<210> SEQ ID NO 89
<211> LENGTH: 499
<212> TYPE: DNA
<213> ORGANISM: Mycobacterium tuberculosis
<220> FEATURE:
<221> NAME/KEY: modified_base
<222> LOCATION: (1)...(499)
<223> OTHER INFORMATION: n = any nucleotide

<400> SEQUENCE: 89

```
gatgcaccgc gaccttgccg acatctggcc ggtgatcgat cgcgacccgg ccgtgcgcgt      60
ggtcttggtc cgcggtgaag gcaangcctt ttcctccggc ggcagtttcg acctgatcgc     120
cgaaaccatc ggcgactacc agggccggct gcgcatcatg cgcgaggccc gcgacctggt     180
gctcaacctg gtcaacttcg acaagccggt ggtgtcggcg attcggggcc cggccgtcgg     240
tgcgggtctg gttgtcgcgc tgctcgccga catttcggtg gcgggccgcg ccgcgaaaga     300
tcatcgatgg gcacaccaaa ctcggggtcg ccgcggggga tcacgcggcg atctgctggc     360
ccctgctggt cggcatggcc aaggccaagt actacctgct gacctgcgaa ccgctgtccg     420
gggaagagcc gaaacgcatc ggtctggtct ccatctgctn cgacgacgac gatgttgctc     480
cccacccgna acacgcctg                                                  499
```

<210> SEQ ID NO 90
<211> LENGTH: 530
<212> TYPE: DNA
<213> ORGANISM: Mycobacterium tuberculosis
<220> FEATURE:
<221> NAME/KEY: modified_base
<222> LOCATION: (1)...(530)
<223> OTHER INFORMATION: n = any nucleotide

<400> SEQUENCE: 90

```
gcggcctgct cgaccgggtg ccgcccgcaa aaaccgacga ngtgcacaag ctcttcgtcg      60
aggaactcgg cgacgagccg gcccggctgt tcgcctcctt cgaggaagag ccgttcgcgt     120
cggcgtccat cgcccaggtg cactacgcga ccctgcgcag cggcgaggag gtggtggtca     180
agatccagcg gccgggcatc cgccgccgcg ttgccgccga cctgcagatc ctcaagcgct     240
```

-continued

```
tcgcgcagac cgtcgaactg gccaagctgg gccggcggct ctcggcacaa gacgtggtcg      300
ccgacttcgc cgacaacctg gccgaggagc tggactttcg cctcgaggcg cagtccatgg      360
gaggcctggg tctcccacct acacgcctcg ccgctgggca aaaacatccg ggtgccgcag      420
gtgcacttgg ggacttcacc accgaagcgg gtgttgacga tggaacgggt tgcacggcat      480
ccgcattcga caacgccgcc gcgatccgca aggccgggtt cgacggtgtc                 530
```

<210> SEQ ID NO 91
<211> LENGTH: 200
<212> TYPE: DNA
<213> ORGANISM: Mycobacterium tuberculosis
<220> FEATURE:
<221> NAME/KEY: modified_base
<222> LOCATION: (1)...(200)
<223> OTHER INFORMATION: n = any nucleotide

<400> SEQUENCE: 91

```
cgttccagga gagcgcagcc cgccgcggat aacgtcacgg ccgtggcggg cagcgcaggt       60
gtcggcccgt catcaggcac gtcggtgccg acgagcggcg gcgaangaac gtggcaacgc      120
cgacgagttc gtcgatatgg actccggccc ggcgattccg ccgtcgggcg agcgggacgc      180
ttgggcgtcc aattcgggcg                                                 200
```

<210> SEQ ID NO 92
<211> LENGTH: 3
<212> TYPE: PRT
<213> ORGANISM: Artificial Sequence
<220> FEATURE:
<223> OTHER INFORMATION: flexible polylinker

<400> SEQUENCE: 92

Gly Cys Gly
 1

<210> SEQ ID NO 93
<211> LENGTH: 6
<212> TYPE: PRT
<213> ORGANISM: Artificial Sequence
<220> FEATURE:
<223> OTHER INFORMATION: flexible polylinker

<400> SEQUENCE: 93

Gly Cys Gly Gly Cys Gly
 1               5

<210> SEQ ID NO 94
<211> LENGTH: 9
<212> TYPE: PRT
<213> ORGANISM: Artificial Sequence
<220> FEATURE:
<223> OTHER INFORMATION: flexible polylinker

<400> SEQUENCE: 94

Gly Cys Gly Gly Cys Gly Gly Cys Gly
 1               5

<210> SEQ ID NO 95
<211> LENGTH: 5
<212> TYPE: PRT
<213> ORGANISM: Artificial Sequence
<220> FEATURE:
<223> OTHER INFORMATION: flexible polylinker

<400> SEQUENCE: 95

-continued

```
Gly Gly Gly Gly Ser
1               5

<210> SEQ ID NO 96
<211> LENGTH: 10
<212> TYPE: PRT
<213> ORGANISM: Artificial Sequence
<220> FEATURE:
<223> OTHER INFORMATION: flexible polylinker

<400> SEQUENCE: 96

Gly Gly Gly Gly Ser Gly Gly Gly Gly Ser
1               5                   10

<210> SEQ ID NO 97
<211> LENGTH: 15
<212> TYPE: PRT
<213> ORGANISM: Artificial Sequence
<220> FEATURE:
<223> OTHER INFORMATION: flexible polylinker

<400> SEQUENCE: 97

Gly Gly Gly Gly Ser Gly Gly Gly Gly Ser Gly Gly Gly Gly Ser
1               5                   10                  15
```